(12) United States Patent
Qing et al.

(10) Patent No.: US 11,673,136 B2
(45) Date of Patent: Jun. 13, 2023

(54) NANOPORE DEVICES FOR SENSING BIOMOLECULES

(71) Applicants: Quan Qing, Chandler, AZ (US); Yuan Wang, Anhui (CN); Joshua Sadar, Gilbert, AZ (US)

(72) Inventors: Quan Qing, Chandler, AZ (US); Yuan Wang, Anhui (CN); Joshua Sadar, Gilbert, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 488 days.

(21) Appl. No.: 15/945,717

(22) Filed: Apr. 4, 2018

(65) Prior Publication Data

US 2018/0280968 A1 Oct. 4, 2018

Related U.S. Application Data

(60) Provisional application No. 62/481,467, filed on Apr. 4, 2017.

(51) Int. Cl.
*B01L 3/00* (2006.01)
*C12Q 1/6869* (2018.01)
(Continued)

(52) U.S. Cl.
CPC ....... *B01L 3/5027* (2013.01); *B01L 3/502707* (2013.01); *B01L 3/502761* (2013.01);
(Continued)

(58) Field of Classification Search
CPC ............ C12Q 1/6869; C12Q 2565/631; C12Q 2565/607; C12Q 2565/629;
(Continued)

(56) References Cited

U.S. PATENT DOCUMENTS 8,961,757 B2    2/2015   Nuckolls et al.
8,968,540 B2    3/2015   Reinhart et al.
(Continued)

FOREIGN PATENT DOCUMENTS

WO    WO2018200965 A1    11/2018
WO    WO2020010029 A1    1/2020
WO    WO2020010029 A9    1/2020

OTHER PUBLICATIONS

Singh et al. (Science Direct, Reference module in Materials Science and Materials Engineering, 2016). (Year: 2016).*

(Continued)

*Primary Examiner* — Dean Kwak
(74) *Attorney, Agent, or Firm* — Lewis Roca Rothgerber Christie LLP

(57) ABSTRACT

The present disclosure provides chips, devices and methods for sequencing a biomolecule. The biomolecule may be DNA, RNA. a protein, or a peptide. The chip comprises a substrate; a first and second fluid chamber; fluid channels connecting the first and second fluid chamber; a first and second electrode disposed on opposing sides of the central fluid channel and having a nanogap therebetween, wherein the width of the nanogap is modulated by confined electrochemical deposition; and a passivation layer disposed on top of the first and second electrodes and the fluid channel.

9 Claims, 15 Drawing Sheets

(51) Int. Cl.
  *G01N 27/327* (2006.01)
  *B82Y 15/00* (2011.01)
  *G01N 33/487* (2006.01)
(52) U.S. Cl.
  CPC ....... *C12Q 1/6869* (2013.01); *G01N 27/3276* (2013.01); *G01N 27/3278* (2013.01); *B01L 2300/0645* (2013.01); *B01L 2300/0896* (2013.01); *B82Y 15/00* (2013.01); *G01N 33/48721* (2013.01)
(58) Field of Classification Search
  CPC ......... G01N 33/48721; G01N 27/3275; G01N 27/3276; G01N 27/3278; B82Y 15/00; B01L 3/5027; B01L 2300/0896; B01L 2200/0663; B01L 2300/0645; B01L 3/502707; B01L 3/502761
  See application file for complete search history.

(56) References Cited

U.S. PATENT DOCUMENTS

| | | | |
|---|---|---|---|
| 9,140,682 | B2 | 9/2015 | Lindsay et al. |
| 9,442,111 | B2 | 9/2016 | Lindsay et al. |
| 10,641,726 | B2 | 5/2020 | Kuo et al. |
| 10,669,579 | B2* | 6/2020 | Bi .................... B81B 1/004 |
| 2009/0215156 | A1* | 8/2009 | Chung ................ B82Y 15/00 430/323 |
| 2010/0066348 | A1* | 3/2010 | Merz .................. C12Q 1/6869 324/71.1 |
| 2010/0084276 | A1* | 4/2010 | Lindsay ............... G01N 27/028 204/403.01 |
| 2014/0190824 | A1* | 7/2014 | Credo .................. B82Y 15/00 204/403.15 |
| 2016/0097759 | A1 | 4/2016 | Lindsay et al. |
| 2016/0108002 | A1 | 4/2016 | Zhang et al. |
| 2016/0177383 | A1 | 6/2016 | Ashcroft et al. |
| 2016/0258925 | A1 | 9/2016 | Gyarfas et al. |
| 2018/0217083 | A1* | 8/2018 | Kuo .................... B81C 1/00547 |

OTHER PUBLICATIONS

Ah, C. et al., "FabricatioA11:A46d nanogap electrodes by surface-catalyzed chemical deposition", Applied Physics Letter, Mar. 2006 [retrieved on Dec. 31, 2018], 88(13), article No. 133116, 3 pages, retrieved from the internet <URL:https://aip.scitation.org/doi/10.1063/1.2190464> <DOI: 10.1063/1.2190464>.

Akahori, R. et al., "Slowing single-stranded DNA translocation through a solid-state nanopore by decreasing the nanopore diameter", Nanotechnology, Jun. 2014 [retrieved on Dec. 31, 2018], 25, article No. 275501, 6 pages, retrieved from the internet <URL:http://iopscience.iop.org/article/10.1088/0957-4484/25/27/275501/meta> <doi:10.1088/0957-4484/25/27/275501>.

Biswas, S. et al., "Universal Readers Based on Hydrogen Bonding or π-π Stacking for Identification of DNA Nucleotides in Electron Tunnel Junctions", ACS Nano, Dec. 2016 [available online Nov. 2016], 10(12), pp. 11304-11316, retrieved from the internet<URL:https://pubs.acs.org/doi/abs/10.1021/acsnano.6b06466> <DOI: 10.1021/acsnano.6b06466>.

Boussaad, S. et al., "Atom-size gaps and contacts between electrodes fabricated with a self-terminated electrochemical method", Applied Physics Letters, Apr. 2002 [available online Mar. 2002, retrieved on Dec. 31, 2018], 80(13), pp. 2398-2400, retrieved from the internet <https://aip.scitation.org/doi/10.1063/1.1465128> <DOI: 10.1063/1.1465128>.

Chang, S. et al., "Electronic Signatures of all Four DNA Nucleosides in a Tunneling Gap", Nano Letters, Mar. 2010 [available online Feb. 2010, retrieved on Dec. 31, 2018], 10(3), pp. 1070-1075, retrieved from the internet <URL: https://pubs.acs.org/doi/abs/10.1021/nl1001185> <DOI: 10.1021/nl1001185>.

Chen, F. et al., "Electrochemical approach for fabricating nanogap electrodes with well controllable separation", Applied Physical Letters, Mar. 2005 [retrieved on Dec. 31, 2018], 86(12), article No. 123105, 3 pages, retrieved from the internet <URL:https://aip.scitation.org/doi/10.1063/1.1871361> <DOI: 10.1063/1.1871361>.

He, J. et al., "Identification of DNA Basepairing via Tunnel-Current Decay", Nano Letters, Dec. 2007 [available online Nov. 2007, retrieved on Dec. 31, 2018], 7(12), pp. 3854-3858, retrieved from the internet <URL:https://pubs.acs.org/doi/abs/10.1021/nl0726205> <DOI: 10.1021/nl0726205>.

He, X. et al., "Electrochemical fabrication of atomically thin metallic wires and electrodes separated with molecular-scale gaps", Journal of Electroanalytical Chemistry, Apr. 2002 [availabe online Mar. 2002, retrieved on Dec. 31, 2018], 522(2), pp. 167-172, retrieved from the internet <https://www.sciencedirect.com/science/article/pii/S0022072802006927> <DOI: 10.1016/S0022-0728(02)00692-7>.

He, Y. et al., "Controlling DNA Translocation through Gate Modulation of Nanopore Wall Surface Charges", ACS Nano, Jul. 2011 [available online Jun. 2011, retrieved on Dec. 31, 2018], 5(7), pp. 5509-5518, <URL:https://pubs.acs.org/doi/10.1021/nn201883b> <DOI: 10.1021/nn201883b>.

Ho, P. et al., "Electromigration in metals", Reports on Progress in Physics, 1989 [retrieved on Dec. 31, 2018], 52(3), pp. 301-348, retrieved from the internet <URL:http://iopscience.iop.org/article/10.1088/0034-4885/52/3/002/meta> <DOI: 10.1088/0034-4885/52/3/002>.

Im, J. et al., "Electronic single-molecule identification of carbohydrate isomers by recognition tunnelling", Nature Communications, Dec. 2016 [retrieved on Dec. 31, 2018], 7, article No. 13868, 7 pages, retrieved from the internet <URL:https//www.nature.com/articles/ncomms13868> <DOI: 10.1038/ncomms13868>.

Jiao, X. et al., "Surgically Implantable 3D Electrodes and Flexible Probes Enabled by Biodegradable Material", Symposium Detail of the 2016 MRS Fall Meeting & Exhibit (Nov. 27-Dec. 2, 2016, Boston, Massachusetts), Session Dec. 2, 2016 [retrieved on Dec. 10, 2018], Abstract BM4.17.01, retrieved from the internet <URL:https://mrs.org/fall2016/fall-2016-symposia/?code=BM4>.

Jiao, X. et al., "Ultra-small flexible bio-probes with biologically degradable sacrificial layer for accurate implantation", Presentation at 2016 MRS Fall Meeting & Exhibit (Nov. 27-Dec. 2, 2016, Boston, Massachusetts), Session Dec. 2, 2016, 14 slides.

Kishnakumar. P. et al., "Slowing DNA Translocation through a Nanopore Using a Functionalized Electrode", ACS Nano, Nov. 2013 [available online Oct. 2013, retrieved on Dec. 31, 2018], 7(11), pp. 10319-10326, retrieved from the internet <URL:https://pubs.acs.org/doi/10.1021/nn404743f> <DOI: 10.1021/nn404743f>.

Li, T. et al., "Nanogap Electrodes", Advanced Materials, Jan. 2010 [available online Jul. 2009, retrieved on Dec. 31, 2018], 22(2), pp. 286-300, retrieved from the internet <URL:https://onlinelibrary.wiley.com/doi/abs/10.1002/adma.200900864> <DOI: 10.1002/adma.200900864>.

Luan, B. et al., "Controlling the motion of DNA in a nanochannel with transversal alternating electric voltages", Nanotechnology, Jun. 2014 [retrieved on Dec. 31, 2018], 25(26), article No. 265101, 7 pages, retrieved from the internet <http://iopscience.iop.org/article/10.1088/0957-4484/25/26/265101/meta> <DOI: 10.1088/0957-4484/25/26/265101>.

Moreland, J. et al., "Electron tunneling experiments using Nb—Sn "break" junctions", Journal of Applied Physics, Nov. 1985 [retrieved on Dec. 31, 2018], 58(10), pp. 3888-3895, retrieved from the internet <https://aip.scitation.org/doi/abs/10.1063/1.335608> <DOI: 10.1063/1.335608>.

Morpurgo, A. et al., "Controlled fabrication of metallic electrodes with atomic separation", Applied Physics Letters, Apr. 1999 [retrieved on Dec. 31, 2018], 74(14), pp. 2084-2086, retrieved from the internet <URL:https://aip.scitation.org/doi/10.1063/1.123765> <DOI: 10.1063/1.123765>.

Nam, S. et al., "Ionic Field Effect Transistors with Sub-10 nm Multiple Nanopores", Nano Letters, May 2009 [available online Apr. 2009, retrieved on Dec. 31, 2018], 9(5), pp. 2044-2048, retrieved from the internet <URL:https://pubs.acs.org/doi/10.1021/nl900309s> <DOI: 10.1021/nl900309s>.

(56) References Cited

OTHER PUBLICATIONS

Park, H. et al., "Fabrication of metallic electrodes with nanometer separation by electromigration", Applied Physics Letters, Jul. 1999 [retrieved on Dec. 31, 2018], 75(2), pp. 301-303, retrieved from the internet <URL:https://aip.scitation.org/doi/10.1063/1.124354> <DOI: 10.1063/1.124354>.
Qing, Q. et al., "Finely Tuning Metallic Nanogap Size with Electrodeposition by Utilizing High-Frequency Impedance in Feedback", Angewandte Chemie, Dec. 2005 [available online Nov. 2005], 44(47), pp. retrieved from the internet<URL:https://onlinelibrary.wiley.com/doi/full/10.1002/anie.200502680> <DOI: 10.1002/anie.200502680>.
Reed, M. et al., "Conductance of a Molecular Junction", Science, Oct. 1997 [retrieved on Dec. 31, 2018], 278(5336), pp. 252-254, retrieved from the internet <URL:http://science.sciencemag.org/content/278/5336/252> <DOI: 10.1126/science.278.5336.252>.
Sadar, J. et al., "Bottom-up preparation of nanopore array with self-aligned nanogap electrodes for single biomolecule characterization", Bulletin of the American Physical Society, Joint Meeting of the Four Corners and Texas Sections of the American Physical Society (Oct. 21-22, 2016, Las Cruces, New Mexico), Session Oct. 22, 2016 [retrieved on Dec. 12, 2018], 61(15), Abstract J2.00004, retrieved from the internet <URL:http://meetings.aps.org/Meeting/TSF16/Event/284500>.
Sadar, J. et al., "Bottom-up preparation of nanopore array with self-aligned transverse electrodes for DNA sequencing", Presentation at Joint Meeting of the Four Corners and Texas Sections of the American Physical Society (Oct. 21-22, 2016, Las Cruces, New Mexico), Session Oct. 22, 2016, 15 slides.
Sadar, J. et al., "Confined Electrochemical Deposition in Sub-15 nm Space for Preparing Nanogap Electrodes", ECS Transactions (Conference Proceedings for 231st ECS Meeting, May 28, 2017-Jun. 1, 2017), 2017 [retrieved on Dec. 31, 2018], 77(6), pp. 65-72, retrieved from the internet <URL:http://ecst.ecsdl.org/content/77/7/65.full.pdf+html> <DOI: 10.1149/07707.0065ecst>.
Sadar, J. et al., "Preparation of a sub-10 nm fluidic system with self-aligned nanogap electrodes for biomolecule characterization", Poster at Biophest 2016 (Apr. 16, 2016, Tucson, Arizona).
Sadar, J. et al., "Preparation of a sub-10 nm fluidic system with self-aligned nanogap electrodes for biomolecule characterization", Poster presented at Annual Meeting of the APS Four Corners Section (Oct. 16-17, 2015, Tempe, Arizona), Poster Session Oct. 16, 2015.
Sadar, J. et al., Preparation of A Sub-10 Nm Fluidic System with Self-Aligned Nanogap Electrodes for Biomolecule Characterization, BioPhest 2016 Abstracts, Biophest 2016 (Apr. 16, 2016, Tuscon, Arizona), retrieved on Dec. 10, 2018, pp. 17-18, retrieved from the internet <URL:https://cbc.arizona.edu/sites/cbc.arizona.edu/files/program_biophest2016_final.pdf>.
Sadar, J. et al., "Sub-10 nm fluidic system with self-aligned nanogap electrodes for biomolecule characterizations", Bulletin of the American Physical Society, Annual Meeting of the APS Four Corners Section (Oct. 16-17, 2015, Tempe, Arizona), Poster Session Oct. 16, 2015 [retrieved on Dec. 10, 2018], 60(11), Abstract F1.00010, retrieved from the internet <URL:http://meetings.aps.org/Meeting/4CF15/Event/258601>.
Sadar, J., "Preparation of a sub-10 nm fluidic system with self-aligned nanogap electrodes for biomolecule characterization", BioPhest 2015 Abstracts, Biophest 2015 (May 2, 2015, Tempe, Arizona), retrieved on Dec. 10, 2018, p. 5, retrieved from the internet <URL:https://becksteinlab.physics.asu.edu/resources/63/biophest-2015-at-asu>.
Sadar, J., "Preparation of a sub-10 nm fluidic system with self-aligned nanogap electrodes for biomolecule characterization", Presentation at Biophest 2015 (May 2, 2015, Tempe, Arizona), 20 slides.
Strachan, D. et al., "Controlled fabrication of nanogaps in ambient environment for molecular electronics", Applied Physics Letters, Jan. 2005 [retrieved on Dec. 31, 2018], 86(4), article No. 043109, 3 pages, retrieved from the internet <https://aip.scitation.org/doi/10.1063/1.1857095> <DOI: 10.1063/1.1857095>.
Tian, J. et al., "The fabrication and characterization of adjustable nanogaps between gold electrodes on chip for electrical measurement of single molecules", Nanotechnology, Jun. 2010 [retrieved on Dec. 31, 2018], 21(27), article No. 274012, 6 pages, retrieved from the internet <URL:http://iopscience.iop.org/article/10.1088/0957-4484/21/27/274012/meta> <DOI: 10.1088/0957-4484/21/27/274012>.
Tsujino, S. et al., "Static and optical field enhancement in metallic nanotips studied by two-photon photoemission microscopy and spectroscopy excited by picosecond laser pulses", Applied Physics Letters, Mar. 2009 [retrieved on Dec. 31, 2018], 94, article No. 093508, 3 pages, retrieved from the internet <URL:https7/aip.scitation.org/doi/10.1063/1.3095480> <DOI: 10.1063/1.3095480>.
Tsutsui, M .et al., "Transverse electric field dragging of DNA in a nanochannel", Scientific Reports, May 2012 [retrieved on Dec. 31, 2018], 2, article No. 394, 7 pages, retrieved from the internet <URL:https://www.nature.com/articles/srep00394> <DOI: 10.1038/srep00394>.
Wanunu, M. et al., "Chemically Modified Solid-State Nanopores", Nano Letters, Jun. 2007 [available online May 2007, retrieved on Dec. 31, 2018], 7(6), pp. 1580-1585, retrieved from the internet <https://pubs.acs.org/doi/10.1021/nl070462b> <DOI: 10.1021/nl070462b>.
Xiang, J. et al., "A Controllable Electrochemical Fabrication of Metallic Electrodes with a Nanometer/Angstrom-Sized Gap Using an Electric Double Layer as Feedback", Angewandte Chemie, Feb. 2005 [available online Jan. 2005, retrieved on Dec. 31, 2018], 44(8), pp. 1265-1268, retrieved from the internet <https://onlinelibrary.wiley.com/doi/full/10.1002/anie.200461797> <DOI: 10.1002/anie.200461797>.
Yanson, A. et al., "Formation and manipulation of a metallic wire of single gold atoms", Nature, Oct. 1998 [retrieved on Dec. 31, 2018], 395, pp. 783-785, retrieved from the internet <https://www.nature.com/articles/27405> <DOI: 10.1038/27405>.
U.S. Appl. No. 16/608,603, filed Oct. 25, 2019.
U.S. Appl. No. 16/675,127, filed Nov. 5, 2019.

* cited by examiner

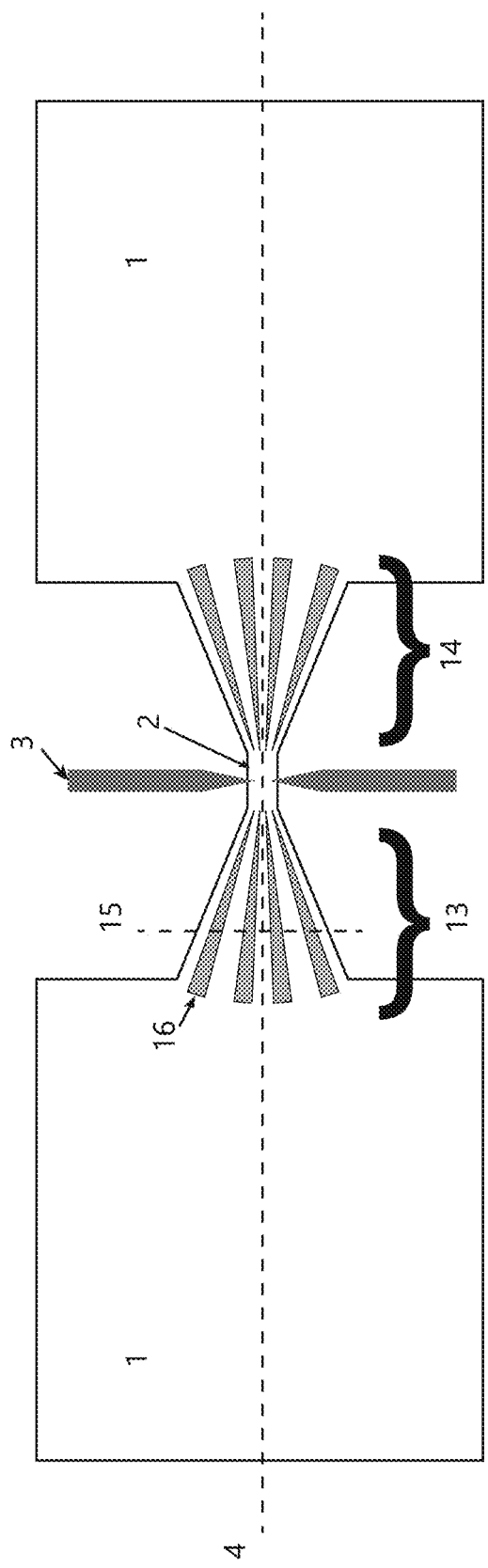

NANOPORE DEVICES FOR SENSING BIOMOLECULES

FEDERALLY SPONSORED RESEARCH OR DEVELOPMENT

This invention was made with government support under R21 HG009363 awarded by the National Institutes of Health. The government has certain rights in the invention.

BACKGROUND

Increasingly faster and cheaper genome sequencing technologies are fundamentally changing biological research and biomedical practices. Although significant improvements have been achieved in the past decade, existing sequencing methods still require relatively long time and high cost to sequence a single genome. Therefore, several third-generation sequencing techniques have been proposed, characterized by single-molecule level readout and high throughput. Nanopore sensing has been the most promising candidate as it requires no complex labeling or DNA amplification, and the long read length could substantially help the alignment and assembly of repetitive DNAs. However, the existing designs of nanopore sensors and the preparation strategies face significant challenges such as the scalability and reproducibility of fabrication, lack of control of translocation, and low specificity in read-out signals.

Citation of any reference in this section is not to be construed as an admission that such reference is prior art to the present disclosure.

SUMMARY

The present disclosure provides an assay chip configured to detect or sequence a biomolecule, such as DNA, RNA, a protein or a peptide. In one embodiment, the assay chip comprises a substrate; a first and second fluid chamber; a first fluid channel; a first and second electrode disposed on opposing sides of the first fluid channel and having a nanogap therebetween, wherein the width of the nanogap is modulated by confined electrochemical deposition; and a passivation layer disposed on top of the first and second electrodes and the fluid channel. In another embodiment, the assay chip comprises a substrate; a first and second fluid chamber; a first fluid channel; a first and second electrode disposed on opposing sides of the first fluid channel and having a nanogap therebetween, wherein the width of the nanogap is modulated by confined electrochemical deposition; a second and a third fluid channels, each comprising a plurality of translocation guidance canals, wherein the second fluid channel connects the first fluid chamber to the first fluid channel and the third fluid channel connects the second fluid chamber to the first fluid channel; and a passivation layer disposed on top of the first and second electrodes and the first, second and third fluid channels.

The present disclosure also provides a device for sensing biomolecules comprising a chip as defined herein; and an integrated circuit configured to detect an electrical current between the first and second electrodes upon passage of the biomolecule through the nanogap.

The present disclosure also provides a device for sensing biomolecules comprising a chip as defined herein; and an integrated circuit configured to detect an electrical current between the chambers on opposing ends of the substrate which are linked by the fluid channel through the nanogap.

The present disclosure also provides a method for forming a chip. The method comprises fabricating a first and a second electrode on a substrate, the first and second electrode having an initial gap therebetween; providing a sacrificial layer on top of the substrate; providing a passivation layer on top the sacrificial layer, the passivation layer having a first and a second opening; fabricating a first and second fluid chamber on opposing ends of the substrate and on top of the passivation layer, each of the first and second fluid chambers having a port for receiving and removing solutions; fabricating a fluid channel between the first and second electrode and connecting the first and second fluid chamber; and depositing a metal on the first and second electrodes within the fluid channel while monitoring impedance, wherein the deposition narrows the initial gap.

The present disclosure also provides a chip prepared by the methods disclosed herein.

The present disclosure also provides a device for sensing biomolecules. The device comprises a chip prepared by the methods disclosed herein; and an integrated circuit configured to detect an electrical current between the first and second electrodes upon passage of the biomolecule through the nanogap.

The present disclosure also provides a device for sensing biomolecules. The device comprises a chip prepared by the methods disclosed herein; and an integrated circuit configured to detect an electrical current between the chambers on opposing ends of the substrate which are linked by the fluid channel through the nanogap.

The present disclosure also provides a method for detecting a biomolecule in a sample. The method comprises providing a device as disclosed herein; passing a biomolecule through the gap; and detecting a signal produced when the biomolecule passes through the gap.

The present disclosure also provides a method for detecting a biomolecule in a sample. The method comprises providing a device as disclosed herein; passing a biomolecule through the gap; and detecting a signal produced when the biomolecule interacts with a first and second reagent.

The present disclosure also provides a method for sequencing a nucleic acid. The method comprises providing a device as disclosed herein; passing a nucleobase through the gap; detecting the signal produced when the nucleobase passes through the gap; from the signal detected in the previous step, identifying the nucleobase of the nucleic acid; repeating the three previous steps; and from the nucleobases identified in the preceding step, determining the sequence of the nucleic acid.

The present disclosure also provides a method for sequencing a nucleic acid. The method comprises providing a device as disclosed herein; passing a nucleobase through the gap; detecting the signal produced when the nucleobase interacts with a first and second reagent; from the signal detected in the previous step, identifying the nucleobase of the nucleic acid; repeating the three previous steps; and from the nucleobases identified in the preceding step, determining the sequence of the nucleic acid.

BRIEF DESCRIPTION OF THE FIGURES

FIG. 2A shows a top view of the primed chip, with (1) a first and second fluid chamber, (2) a first fluid channel, (3) initial first and second electrode tips, (4) cross-section line for FIG. 2B, and (5) cross-section line for FIG. 3A-FIG. 3C.

FIG. 3A shows the starter-kit chip before etching of the first sacrificial layer, showing (7) substrate, (3) initial first and second electrode tips, (8) first sacrificial layer, and (9) passivation layer. FIG. 3B shows the primed chip after sacrificial layer etching, showing (2) a first fluid channel formed by etching of the sacrificial layer. FIG. 3C shows the assay chip after electrochemical deposition, showing (12) first and second electrode tips with the narrowed nanopore channel in between.

FIG. 4A shows schematic diagrams of a primed chip comprising a second sacrificial layer according to a second and third embodiment of the present disclosure. FIG. 4A shows a top view of the primed chip, after etching of the sacrificial layers, showing (1) first and second fluid chambers, (2) first fluid channel, (3) initial first and second electrode tips, (13) and (14) second and third fluid channels with translocation guidance canals, connecting to (2) first fluid channel; (4) cross-section line for FIG. 4B and FIG. 4D; (15) cross-section line for FIG. 4C and FIG. 4E; and (16) a plurality of supporting walls supporting the translocation guidance canals within the second and third fluid channels.

DETAILED DESCRIPTION

Figures 1A, 1B, 1C:
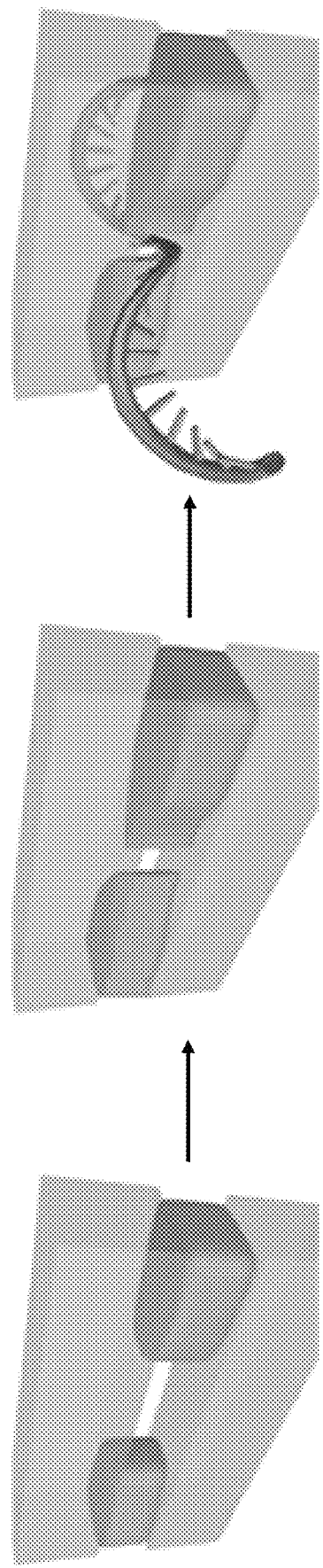
FIG. 1A-FIG. 1C shows the design schematic diagram of an exemplary embodiment of a nanopore device according to the present disclosure, consisting of (FIG. 1A) mass production of starter-kit devices with a thin but wider gap between electrodes confined between dielectric surfaces, (FIG. 1B) in-situ preparation and fine tuning of critical dimensions of the channel onsite to form the nanopore embedded in the self-aligned electrodes, and (FIG. 1C) use of the freshly prepared nanopore devices in biomolecule sensing applications.

In certain embodiments, the invention includes the following:

(1.) A starter-kit chip comprising:
 (a) a substrate;
 (b) a first and second fluid chamber;
 (c) a first sacrificial layer disposed on top of the substrate;
 (d) an initial first and second electrode disposed on opposing sides of the first sacrificial layer and having a gap therebetween; and
 (e) a passivation layer disposed on top of the first and second electrodes and the first sacrificial layer.

(2.) A primed chip comprising:
 (a) a substrate;
 (b) a first and second fluid chamber;
 (c) a first fluid channel connecting the first and second fluid chambers;
 (d) an initial first and second electrode disposed on opposing sides of the first fluid channel and having a gap therebetween; and
 (e) a passivation layer disposed on top of the first and second electrodes and the first fluid channel.

(3.) An assay chip comprising
 (a) a substrate;
 (b) a first and second fluid chamber;
 (c) a first fluid channel connecting the first and second fluid chamber;
 (d) a first and second electrode disposed on opposing sides of the first fluid channel and having a nanogap therebetween, wherein the width of the nanogap is modulated by confined electrochemical deposition; and
 (e) a passivation layer disposed on top of the first and second electrodes and the first fluid channel.

(4.) A starter-kit chip comprising:
 (a) a substrate;
 (b) a first and second fluid chamber;
 (c) a first sacrificial layer and a second sacrificial layer disposed on top of the substrate, wherein the first sacrificial layer is disposed between a first region and a second region of the second sacrificial layer;
 (d) an initial first and second electrode disposed on opposing sides of the first sacrificial layer and having a gap therebetween; and
 (e) a passivation layer disposed on top of the first and second electrodes and the first and second sacrificial layers.

(5.) The starter-kit chip according to the above (4.), wherein the first and second sacrificial layer are fully disposed on top of the substrate.

(6.) The starter-kit chip according to the above (4.), wherein the first sacrificial layer is fully disposed on top of the substrate and the second sacrificial layer is partially disposed on top of the substrate.

(7.) A primed chip comprising:
 (a) a substrate;
 (b) a first and second fluid chamber;
 (c) a first fluid channel;
 (d) an initial first and second electrode disposed on opposing sides of the first fluid channel and having a gap therebetween; and
 (e) a second and third fluid channel, each comprising a plurality of translocation guidance canals, wherein the second fluid channel connects the first fluid chamber to the first fluid channel and the third fluid channel connects the second fluid chamber to the first fluid channel; and
 (f) a passivation layer disposed on top of the first and second electrodes and the first, second, and third fluid channels.

(8.) An assay chip comprising
 (a) a substrate;
 (b) a first and second fluid chamber;
 (c) a first fluid channel;
 (d) a first and second electrode disposed on opposing sides of the first fluid channel and having a nanogap therebetween, wherein the width of the nanogap is modulated by confined electrochemical deposition;
 (e) a second and third fluid channel, each having a plurality of translocation guidance canals, wherein the second fluid channel connects the first fluid chamber to the first fluid channel and the third fluid channel connects the second fluid chamber to the first fluid channel; and
 (f) a passivation layer disposed on top of the first and second electrodes and the first, second, and third fluid channels.

(9.) The chip of the above (3.) or (8.), wherein the narrowed gap has a width of about 1 nm to about 20 nm.

(10.) The chip of the above (3.) or (8.), wherein the narrowed gap has a width of about 1 nm to about 10 nm.

(11.) The chip of the above (3.) or (8.), wherein the narrowed gap has a width of about 2 nm to about 3 nm or about 2.4 nm to 2.6 nm.

(12.) The chip of any of the above (1.) to (11.), wherein the substrate comprises a material selected from the group of consisting of glass, quartz, silicon and combinations thereof.

(13.) The chip of the above (12.), wherein the substrate is a coated glass substrate.

(14.) The chip of the above (13.), wherein the glass substrate is coated with silicon dioxide or silicon nitride.

(15.) The chip of any one of the above (1.) to (14.), wherein the first and second fluid chamber comprise a material capable of bonding to the surface of the substrate and the first and second electrodes.

(16.) The chip of the above (15.), wherein the first and second fluid chamber comprise a material selected from the group consisting of polydimethylsiloxane, epoxy, silica and combinations thereof.

(17.) The chip of any one of the above (1.) to (16.), wherein the first and second electrode comprise a metal, selected from the group consisting of gold, palladium, and platinum and combinations thereof.

(18.) The chip of any one of the above (1.) to (16.), wherein the first and second electrode comprise gold.

(19.) The chip of any one of the above (1.) to (18.), wherein the passivation layer comprises a material selected from the group consisting of silicon dioxide, silicon nitride, hafnium oxide, zirconium dioxide, aluminum oxide, titanium oxide, SU-8 polymer, and combinations thereof.

(20.) The chip of any one of the above (3.) or (8.) to (19.), wherein a first reagent is attached to the first electrode and a second reagent is attached to the second electrode, wherein the first and the second reagent are capable of interacting with a biomolecule.

(21.) The chip of the above (20.), wherein the biomolecule is DNA, RNA, a protein, or a peptide.

(22.) A device for sensing biomolecules comprising:
(a) a chip as defined in any one of the above (3.) or (8.) to (21.); and
(b) an integrated circuit configured to detect an electrical current between the first and second electrodes upon passage of the biomolecule through the nanogap.

(23.) The device of the above (22.), further comprising a detector for measuring the electrical current.

(24.) A device for sensing biomolecules comprising:
(a) a chip as defined in any one of the above (3.) or (8.) to (21.); and
(b) an integrated circuit configured to detect an electrical current between the first and second fluid chambers upon passage of the biomolecule through the nanogap.

(25.) The device of the above (24.), further comprising a detector for measuring the electrical current.

(26.) The device of any one of the above (22.) to (25.), further comprising a system for introducing and removing solutions from the first and second fluid chambers.

(27.) The device of any one of the above (22.) to (26.), further comprising a system for analyzing the electrical current.

(28.) A method for forming a chip, the method comprising
(a) fabricating a first and a second electrode on a substrate, the first and second electrode having an initial gap therebetween;
(b) providing a first sacrificial layer on top of the substrate;
(c) providing a passivation layer on top of the sacrificial layer, the passivation layer having a first and a second opening;
(d) fabricating a first and second fluid chamber on opposing ends of the substrate and on top of the passivation layer, each of the first and second fluid chambers having a port for receiving and removing solutions;
(e) fabricating a first fluid channel between the first and second electrode and connecting the first and second fluid chamber; and
(f) depositing a metal on the first and second electrodes within the fluid channel while monitoring impedance, wherein the deposition narrows the initial gap.

(29.) The method of the above (28.), wherein the initial gap has a width of about 100 nm to about 1 μm.

(30.) The method of the above (28.) or (29.), wherein the narrowed gap has a width of about 1 nm to about 20 nm.

(31.) The method of the above (28.) or (29.), wherein the narrowed gap has a width of about 1 nm to about 10 nm.

(32.) The method of the above (28.) or (29.), wherein the narrowed gap has a width of about 2 nm to about 3 nm or about 2.4 nm to 2.6 nm.

(33.) The method of any one of the above (28.) to (32.), wherein the metal is gold.

(34.) The method of any one of the above (28.) to (32.), wherein the metal is palladium (35.) The method of any one of the above (28.) to (32.), wherein the metal is platinum.

(36.) The method of any one of the above (28.) to (35.), wherein the substrate comprises a material selected from the group of consisting of glass, quartz, silicon and combinations thereof.

(37.) The method of the above (36.), wherein the substrate is a coated glass substrate.

(38.) The method of the above (37.), wherein the glass substrate is coated with silicon dioxide or silicon nitride.

(39.) The method of any one of the above (28.) to (38.), wherein the first and second chamber comprise a material selected from the group consisting of polydimethylsiloxane, epoxy, silica and combinations thereof.

(40.) The method of any one of the above (28.) to (39.), wherein the passivation layer comprises a material selected from the group consisting of silicon dioxide, silicon nitride, hafnium oxide, zirconium dioxide, aluminum oxide, titanium oxide, SU-8 polymer, and combinations thereof.

(41.) The method of any one of the above (28.) to (40.), wherein a first reagent is attached to the first electrode and a second reagent is attached to the second electrode, wherein the first and the second reagent are capable of interacting with a biomolecule.

(42.) The method of any one of the above (28.) to (41.), wherein step (e) comprises removing the first sacrificial layer.

(43.) The method of the above (42.), wherein step (e) comprises removing the first sacrificial layer by etching.

(44.) The method of any one of the above (28.) to (43.), wherein step (f) comprises (i) applying a bias between the first and second electrode and a counter electrode in the presence of metal ions.

(45.) The method of the above (44.), wherein step (f) further comprises (ii) reversing the polarity of the bias applied between the first and second electrode and the counter electrode.

(46.) The method of the above (44.) or (45.), further comprising a reference electrode.

(47.) A method for forming a chip, the method comprising
(a) fabricating a first and a second electrode on a substrate, the first and second electrode having an initial gap therebetween;
(b) providing a first sacrificial layer on top of the substrate;
(c) providing a second sacrificial layer on opposing ends of the first sacrificial layer.
(d) providing a passivation layer on top of the first and second sacrificial layers, the passivation layer having a first and a second opening;
(e) fabricating a first and second fluid chamber on opposing ends of the substrate and on top of the passivation layer, each of the first and second fluid chambers having a port for receiving and removing solutions;
(f) fabricating a first fluid channel between the first and second electrode;
(g) fabricating a second fluid channel connecting the first fluid chamber to the first fluid channel and a third fluid channel connecting the second fluid chamber to the first fluid channel; and
(h) depositing a metal on the first and second electrodes within the fluid channel while monitoring impedance, wherein the deposition narrows the initial gap.

(48.) The method of the above (47.), wherein the initial gap has a width of about 100 nm to about 1 μm.

(49.) The method of the above (47.) or (48.), wherein the narrowed gap has a width of about 1 nm to about 20 nm.

(50.) The method of the above (47.) or (48.), wherein the narrowed gap has a width of about 1 nm to about 10 nm.

(51.) The method of the above (47.) or (48.), wherein the narrowed gap has a width of about 2 nm to about 3 nm or about 2.4 nm to 2.6 nm.

(52.) The method of any one of the above (47.) to (51.), wherein the metal is gold.

(53.) The method of any one of the above (47.) to (51.), wherein the metal is palladium (54.) The method of any one of the above (47.) to (51.), wherein the metal is platinum.

(55.) The method of any one of the above (47.) to (54.), wherein the substrate comprises a material selected from the group of consisting of glass, quartz, silicon and combinations thereof.

(56.) The method of the above (55.), wherein the substrate is a coated glass substrate.

(57.) The method of the above (56.), wherein the glass substrate is coated with silicon dioxide or silicon nitride.

(58.) The method of any one of the above (47.) to (57.), wherein the first and second chamber comprise a material selected from the group consisting of polydimethylsiloxane, epoxy, silica and combinations thereof.

(59.) The method of any one of the above (47.) to (58.), wherein the passivation layer comprises a material selected from the group consisting of silicon dioxide, silicon nitride, hafnium oxide, zirconium dioxide, aluminum oxide, titanium oxide, SU-8 polymer, and combinations thereof.

(60.) The method of any one of the above (47.) to (59.), wherein a first reagent is attached to the first electrode and a second reagent is attached to the second electrode, wherein the first and the second reagent are capable of interacting with a biomolecule.

(61.) The method of any one of the above (47.) to (60.), wherein step (f) comprises removing the first sacrificial layer.

(62.) The method of the above (61.), wherein step (f) comprises removing the first sacrificial layer by etching.

(63.) The method of any one of the above (47.) to (62.), wherein step (g) comprises removing the second sacrificial layer.

(64.) The method of the above (63.), wherein step (g) comprises removing the second sacrificial layer by etching.

(65.) The method of any one of the above (47.) to (64.), wherein step (h) comprises (i) applying a bias between the first and second electrode and a counter electrode in the presence of metal ions.

(66.) The method of the above (65.), wherein step (h) further comprises (ii) reversing the polarity of the bias applied between the first and second electrode and the counter electrode.

(67.) The method of the above (65.) or (66.), further comprising a reference electrode.

(68.) The chip prepared by the method of any one of the above (28.) to (67.).

(69.) A device for sensing biomolecules, the device comprising:
 (a) a chip as defined in the above (68.); and
 (b) an integrated circuit configured to detect an electrical current between the first and second electrodes upon passage of a biomolecule through the nanogap.

(70.) The device of the above (69.), further comprising a detector for measuring the electrical current.

(71.) A device for sensing biomolecules, the device comprising:
 (a) a chip as defined in the above (68.); and
 (b) an integrated circuit configured to detect an electrical current between the first and second fluid chambers upon passage of a biomolecule through the nanogap.

(72.) The device of the above (71.), further comprising a detector for measuring the electrical current.

(73.) The device of any one of the above (69.) to (72.), further comprising a system for introducing and removing solutions from the first and second fluid chambers.

(74.) The device of any one of the above (69.) to (73.), further comprising a system for analyzing the electrical current.

(75.) A method for detecting a biomolecule in a sample, the method comprising
 (a) providing a device of any one of the above (22.) to (27.) or (69.) to (74.);
 (b) passing a biomolecule through the gap; and
 (c) detecting a signal produced when the biomolecule passes through the gap.

(76.) A method for detecting a biomolecule in a sample, the method comprising
 (a) providing a device of any one of the above (22.) to (27.) or (69.) to (74.);
 (b) passing a biomolecule through the gap; and
 (c) detecting a signal produced when the biomolecule interacts with the first and second reagent.

(77.) The method of the above (75.) or (76.), wherein step (b) comprises modulating the potential bias between the first and second electrodes of the device.

(78.) The method of any one of the above (75.) to (77.), wherein step (c) comprises detecting an electrical current between the first and the second electrodes.

(79.) The method of any one of the above (75.) to (77.), wherein step (c) comprises detecting an electrical current between the first and the second fluid chambers.

(80.) A method for sequencing a biomolecule, the method comprising
 (a) providing a device of any one of the above (22.) to (27.) or (69.) to (74.);
 (b) passing a unit of the biomolecule through the gap;
 (c) detecting the signal produced when the unit of the biomolecule passes through the gap;
 (d) from the signal detected in (c), identifying the unit of the biomolecule;
 (e) repeating steps (b) through (d); and
 (f) from the units identified in (d), determining the sequence of the biomolecule.

(81.) A method for sequencing a biomolecule, the method comprising
 (a) providing a device of any one of the above (22.) to (27.) or (69.) to (74.);
 (b) passing a unit of the biomolecule through the gap;
 (c) detecting the signal produced when the unit of the biomolecule interacts with the first and second reagent;
 (d) from the signal detected in (c), identifying the unit of the biomolecule;
 (e) repeating steps (b) through (d); and
 (f) from the units identified in (d), determining the sequence of the biomolecule.

(82.) The method of the above (80.) or (81.), wherein step (b) comprises modulating the potential bias between the first and second electrodes of the device.

(83.) The method of any one of the above (80.) to (82.), wherein step (c) comprises detecting an electrical current between the first and the second electrodes.

(84.) The method of any one of the above (80.) to (82.), wherein step (c) comprises detecting an electrical current between the first and the second fluid chambers.

(85.) The method of any one of the above (80.) to (84.), wherein the biomolecule is DNA.

(86.) The method of any one of the above (80.) to (84.), wherein the biomolecule is RNA.
(87.) The method of any one of the above (80.) to (84.), wherein the biomolecule is a protein.
(88.) The method of any one of the above (80.) to (84.), wherein the biomolecule is a peptide.

Definitions

Unless defined otherwise, all technical and scientific terms used herein have the same meaning as those commonly understood by one of ordinary skill in the art to which this invention belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

Design of Device According to One or More Exemplary Embodiments

In contrast to most existing designs of solid-state nanopores, where the devices are commonly fabricated by drilling a nanoscale orifice through a thin membrane, the present disclosure provides an in-plane nanopore structure, and more importantly, in certain embodiments the present disclosure separates the fabrication of the nanopore structure into three stages. In the first stage, a mass-produced array of a "starter-kit" chip is fabricated by top-down lithography, where two reservoirs are placed on each side of a pair of metal electrodes. The low cost "starter-kit" chip can be shipped directly to the end user (FIG. 1A). In the second and third stages, and in certain embodiments, before the actual sequencing experiments, the user will need to "prepare" the chip to finalize the solid-state nanopore chip (FIG. 1B). In the second stage, the "primed" chip is fabricated by etching the sacrificial layer to form the fluid channel connecting the fluid chambers. In the third stage, with an automated feed-back control system, the gap between each pair of electrodes is narrowed down by a reversible, linearly tunable electrode-position process within a confined nanoscale cavity to form the final nanopore channel that connects the two reservoirs. This fabrication design ensures that the nanopore channel self-aligns with the electrodes, which allows the electrodes to serve both as translocation control and as recognition tunneling signal read-out. Since the feed-back signal used in this preparation process is directly related to the ionic conductance and the tunneling characteristics of the nanogap, the final quality of the nanopore can be reproducibly evaluated and optimized in-situ for immediate sequencing experiments. FIG. 1C shows the use of the nanopore device in a biomolecule sensing application.

Figure 2A:
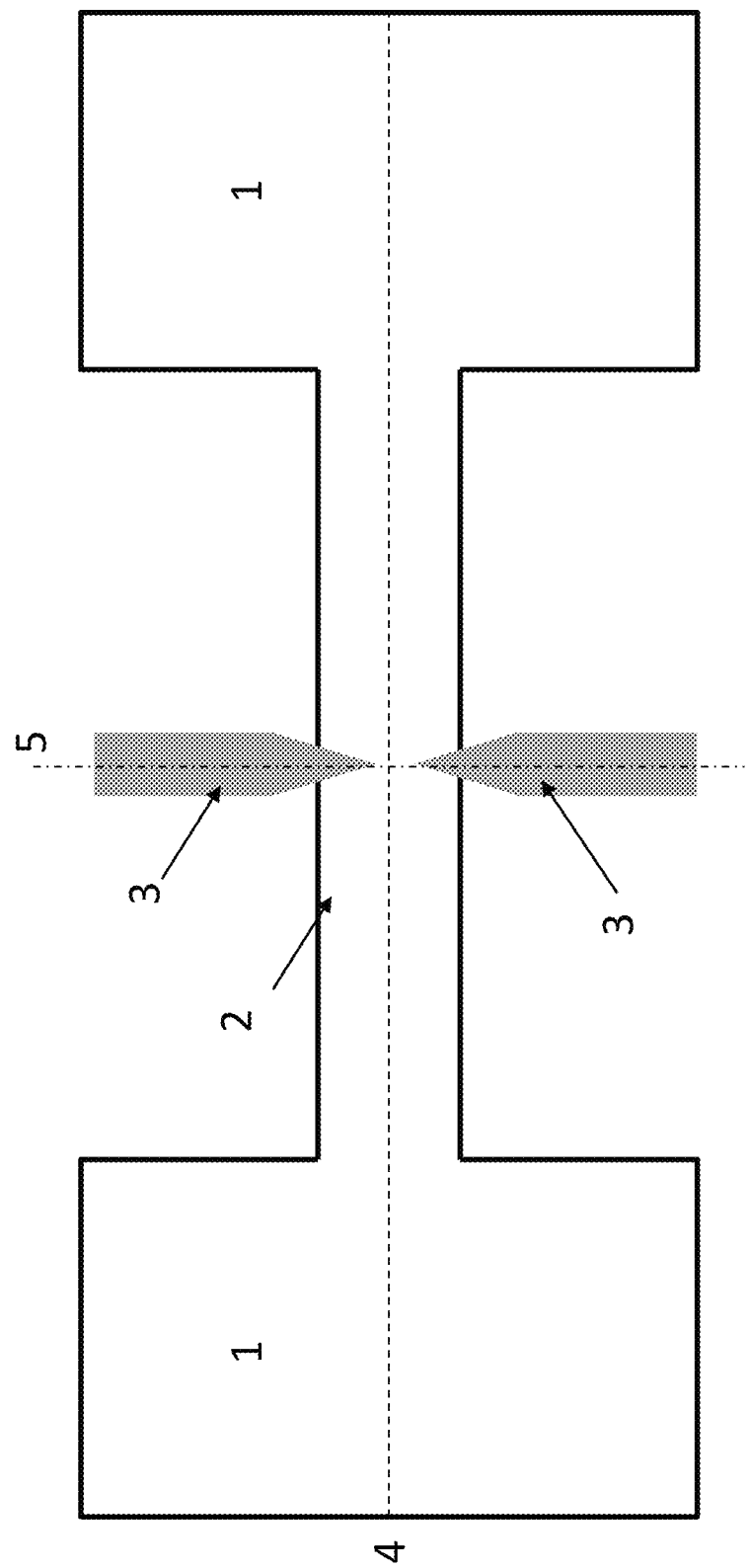
FIG. 2A shows a schematic diagram of a primed chip according to a first embodiment of the present disclosure.
Figure 2B:
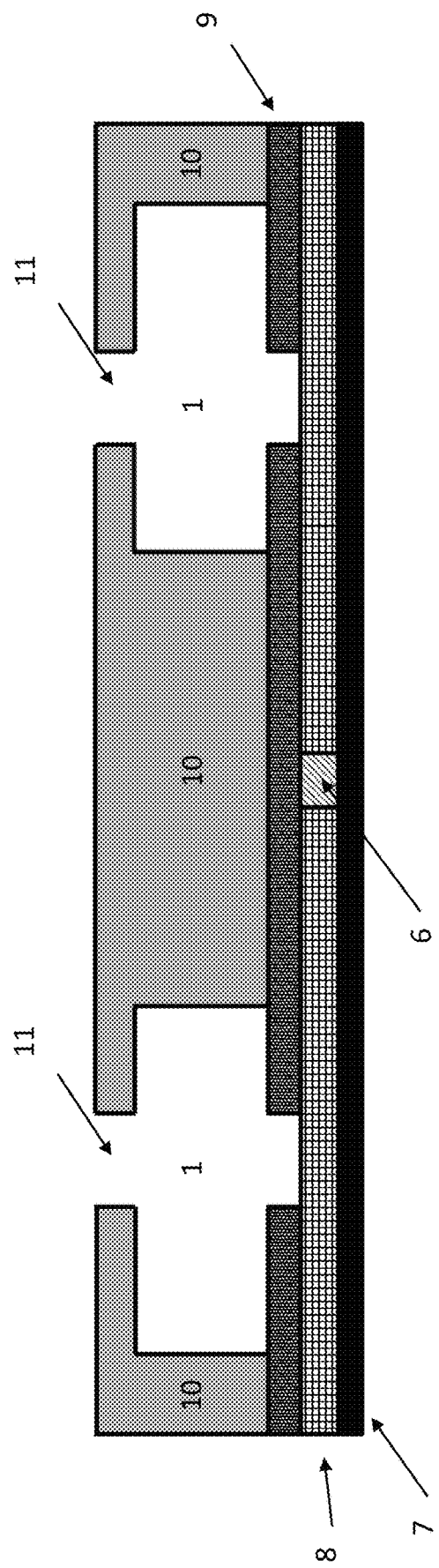
FIG. 2B shows a cross-section schematic diagram of a starter-kit chip before etching of the sacrificial layer, showing (6) position of the initial first and second electrode tips, (7) substrate, (8) first sacrificial layer, (9) passivation layer, (10) PDMS layer, (1) the first and second fluid chambers, and (11) ports for introducing and removing solutions from the first and second fluid chambers.
Figure 3A:
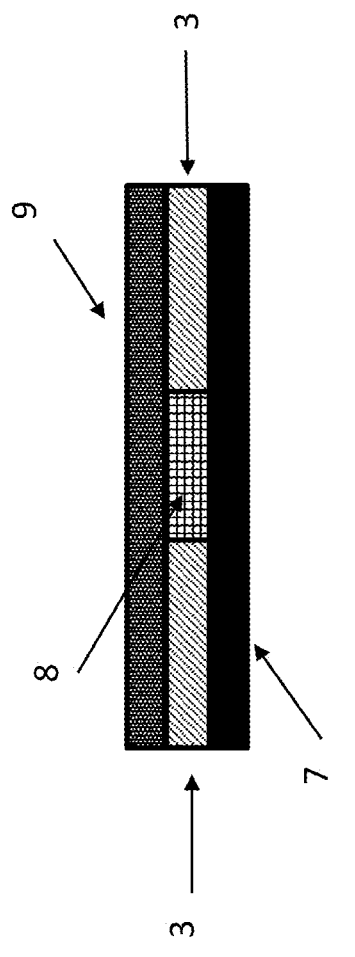
FIG. 3A-FIG. 3C show a cross-section schematic diagram of the formation of the assay chip via the starter-kit chip and primed chip according to one embodiment of the disclosure.

Thus, according to a first embodiment, the present disclosure provides a starter-kit chip comprising one sacrificial layer. In particular, the starter-kit chip comprises (a) substrate; (b) a first sacrificial layer disposed on top of the substrate; (c) a first and second fluid chamber; (d) an initial first and second electrode disposed on opposing sides of the first sacrificial layer and having a gap therebetween; and (e) a passivation layer disposed on top of the first and second electrodes and the first sacrificial layer (FIG. 2B and FIG. 3A).

Figure 3B:
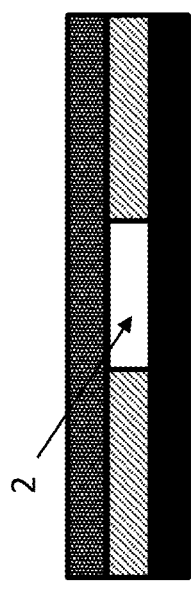

According to a second embodiment, the present disclosure provides a "primed" chip, in which the first sacrificial layer of the starter-kit chip has been removed. The "primed" chip comprises (a) substrate; (b) a first and second fluid chamber; (c) a first fluid channel connecting the first and second fluid chambers; (d) an initial first and second electrode disposed on opposing sides of the fluid channel and having a gap therebetween; and (e) a passivation layer disposed on top of the first and second electrodes and the first fluid channel (FIG. 2A and FIG. 3B).

Figure 3C:
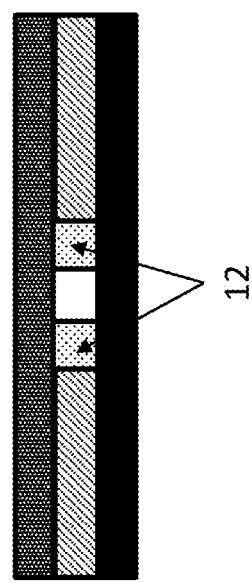

According to a third embodiment, the present disclosure provides a "assay" chip device in which the gap between the initial first and second electrodes of the "primed" chip has been removed by electrochemical deposition The "assay" chip comprises (a) substrate; (b) a first and second fluid chamber; (c) a first fluid channel connecting the first and second fluid chamber; (d) a first and second electrode disposed on opposing sides of the fluid channel and having a nanogap therebetween, wherein the width of the nanogap is modulated by confined electrochemical deposition; and (e) a passivation layer disposed on top of the first and second electrodes and the fluid channel (FIG. 3C).

Figure 4B:
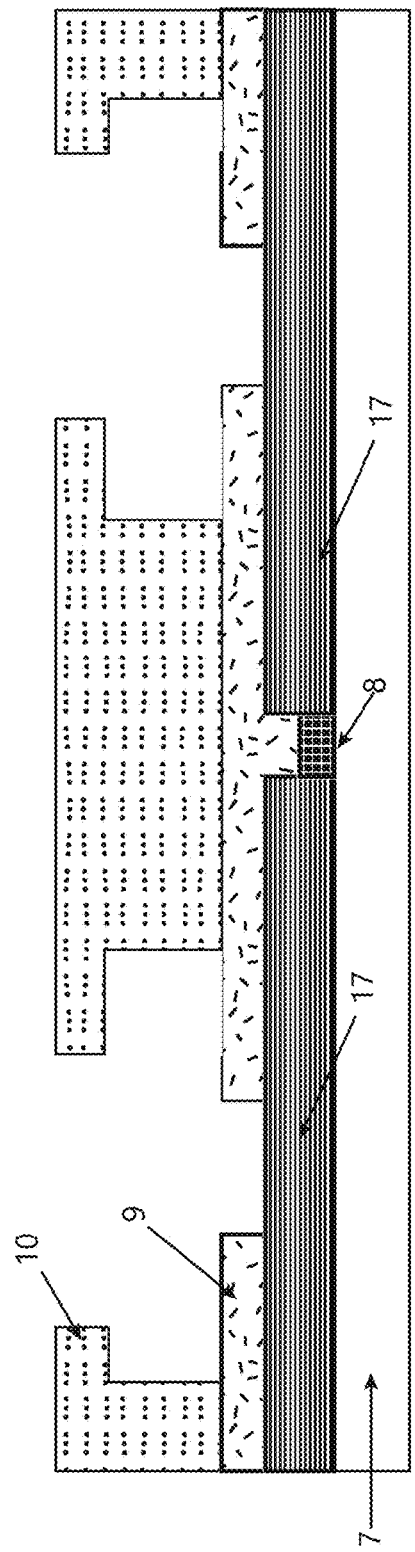
FIG. 4B shows the cross-section schematic diagram of a starter-kit chip, across line (4) of FIG. 4A, before etching of the first and second sacrificial layers according to a first aspect of this embodiment, showing (10) PDMS layer, (9) passivation layer, (7) substrate, (17) second sacrificial layer, and (8) first sacrificial layer. Both the first and second sacrificial layer are disposed on top of the substrate. The plurality of supporting walls for the translocation guidance canals shown in FIG. 4A are not visible in this cross-section.
Figure 4C:
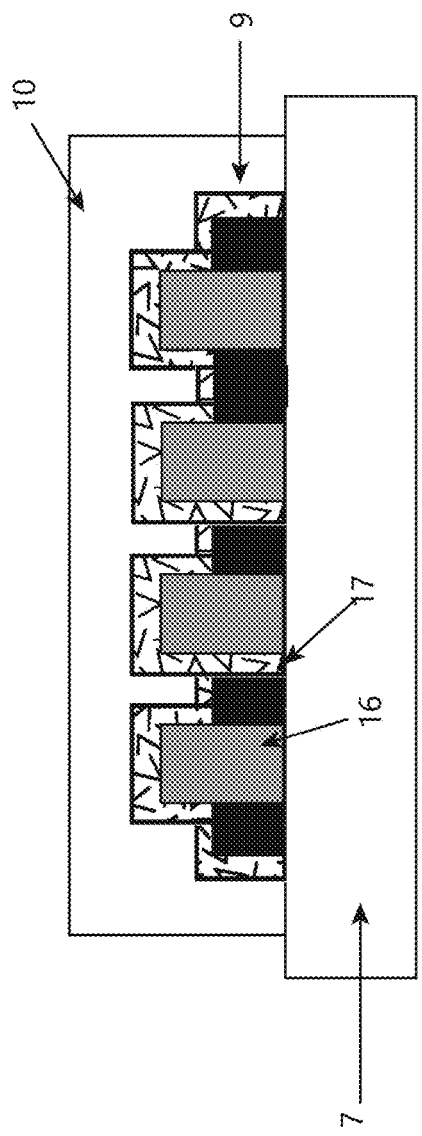
FIG. 4C shows the cross-section schematic diagram of a starter-kit chip across line (15) of FIG. 4A, according to the first aspect of this embodiment, before etching of the first and second sacrificial layers, showing (10) PDMS layer, (9) passivation layer, (7) substrate, (17) second sacrificial layer, and (16) plurality of supporting walls defined by lithography and deposition of dielectric materials.

According to a fourth embodiment, the present disclosure provides a starter-kit chip comprising a first and a second sacrificial layer. In particular, the starter-kit chip comprises (a) substrate; (b) a first sacrificial layer and a second sacrificial layer disposed on top of the substrate, wherein the first sacrificial layer is disposed between a first region and a second region of the second sacrificial layer; (c) an initial first and second electrode disposed on opposing sides of the first sacrificial layer and having a gap therebetween; and (d) a passivation layer disposed on top of the first and second electrodes and the first and second sacrificial layers (FIG. 4B and FIG. 4C).

In a first aspect of this embodiment, the first and second sacrificial layer are disposed on top of the substrate. In this aspect, the second sacrificial layer is thicker than the first sacrificial layer (FIG. 4B).

The thickness of the second sacrificial layer ranges between about 10 nm to about 2000 nm, with optimal thickness between about 100 nm to about 500 nm. The thickness of the first sacrificial layer ranges between about 1 nm to about 50 nm, with optimal thickness between about 2 nm to about 10 nm.

Figure 4D:
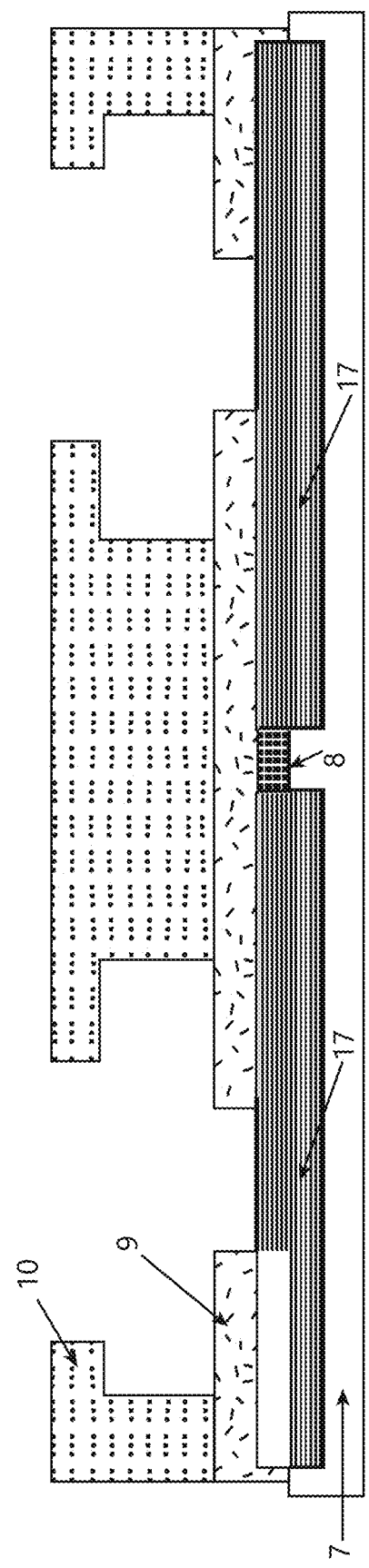
FIG. 4D shows the cross-section schematic diagram of the starter-kit chip across line (4) of FIG. 4A, according to a second aspect of this embodiment, before etching of the first and second sacrificial layers, showing (10) PDMS layer, (9) passivation layer, (7) substrate, (17) second sacrificial layer, and (8) first sacrificial layer. The plurality of supporting walls for the translocation guidance canals are not visible in this cross-section.

In a second aspect of this embodiment, the second sacrificial layer is disposed partially on top of substrate. The height of the second sacrificial layer above the substrate and the height of the first sacrificial layer is substantially the same. In this aspect, the second sacrificial layer is constructed by first patterned etching down into the substrate and then refilling with a sacrificial material (FIG. 4D). The thickness of the first and second sacrificial layers are as described in the preceding paragraph.

The starter-kit chip depicted in FIG. 4D advantageously provides high rigidity to the plurality of supporting walls within the translocation guidance canals in the assay chip.

According to fifth embodiment, the present disclosure provides a "primed" chip, in which the first sacrificial layer of the starter-kit chip has been removed. The "primed" chip comprises (a) substrate; (b) a first and second fluid chamber;

(c) a first fluid channel; (d) an initial first and second electrode disposed on opposing sides of the first fluid channel and having a gap therebetween; (e) a second and a third fluid channels, each comprising a plurality of translocation guidance canals, wherein the second fluid channel connects the first fluid chamber to the first fluid channel and the third fluid channel connects the second fluid chamber to the first fluid channel; and (f) a passivation layer disposed on top of the first and second electrodes and the first, second and third fluid channels (FIG. 4A).

According to sixth embodiment, the present disclosure provides an "assay" chip, in which the first sacrificial layer of the starter-kit chip has been removed. The "assay" chip comprises (a) substrate; (b) a first and second fluid chamber; (c) a first fluid channel; (d) a first and second electrode disposed on opposing sides of the first fluid channel and having a nanogap therebetween, wherein the width of the nanogap is modulated by confined electrochemical deposition; (e) a second and a third fluid channels, each comprising a plurality of translocation guidance canals, wherein the second fluid channel connects the first fluid chamber to the first fluid channel and the third fluid channel connects the second fluid chamber to the first fluid channel; and (f) a passivation layer disposed on top of the first and second electrodes and the first, second and third fluid channels (FIG. 4A).

In each of the chips described herein, the first and second electrodes may comprise a reagent that is capable of selectively interacting with a unit of a biomolecule. In one embodiment, the first and second electrodes may be functionalized with the same reagent, a combination of reagents in a second embodiment, or individually functionalized with different reagents in a third embodiment. Suitable reagents are known in the art and include, without limitation, those disclosed in U.S. Pat. No. 9,442,111 B2; US 20160258925 A1; US 20160177383 A1; U.S. Pat. No. 9,140,682 B2; U.S. Pat. No. 8,968,540 B2; U.S. Pat. No. 8,961,757 B2; US 20160108002 A1; Chang, S. et al. Electronic Signatures of all Four DNA Nucleosides in a Tunneling Gap. Nano Lett. 10, 1070-1075 (2010); Im, J. et al. Electronic single-molecule identification of carbohydrate isomers by recognition tunnelling. Nat. Commun. 7, 13868 (2016); Krishnakumar, P. et al. Slowing DNA Trans location through a Nanopore Using a Functionalized Electrode. ACS Nano 7, 10319-10326 (2013); Wanunu, M. & Meller, A. Chemically modified solid-state nanopores. Nano Lett. 7, 1580-1585 (2007); Biswas, S. et al. Universal Readers Based on Hydrogen Bonding or π-π Stacking for Identification of DNA Nucleotides in Electron Tunnel Junctions. ACS Nano 10, 11304-11316 (2016).

In one embodiment, the reagents are selected from 1-(2-mercaptoethyl)-1H-pyrrole-3-carboxamide (Pr), 5-mercapto-1H-benzo[d]imidazole-2-carboxamide (Bz), 3-(2-mercaptoethyl)-1H-1,2,4-triazole-5-carboxamide (Tz) and 1-(2-Mercaptoethyl)-pyrene (Py).

In another embodiment, the reagent is 4(5)-(2-mercaptoethyl)-1H imidazole-2-carboxamide.

In another embodiment, the reagents are selected from the group consisting of mercaptobenzoic acid, 4-mercaptobenzamide, imidazole-2-carboxide, and dithiocarbamateimidazole-2-carboxide.

In another embodiment, the reagents are selected from the group consisting of 4-mercaptobenzcarbamide, imidazole-2-carboxide, and 4-carbamonylphenyldithiocarbamate.

In another embodiment, the reagents are selected from the group consisting of 5-mercaptouracil (Adenine readers), 8-Mercaptoguanine, S-aminopyridone and 2-N-acetyl-3-deazaguanine (Cytosine Readers), 6-Mercaptocytosine, 5-mercaptocytosine, 5-mercapto-1-methylcytosine, 6-mercapto-1-methylcytosine, and 1-(2-mercaptoethyl)cytosine (Guanine Readers), 2-amino-8-mercaptoadenine, 2,6-Diacetamido-4-mercaptopyridine, 7-aminopropargyl-7-deaza-2-aminoadenine (Thymine Readers), and 5-(2-aminoethyl)-1H-imidazole-2-carboxamide (universal reader).

In another embodiment, the reagents are selected from the group consisting of 1,8 napthyridine and 1,10-Phenanthroline derivates (A-T, T-A base pair readers) and cinnoline derivatives (G-C, C-G base pair readers).

In another embodiment, the reagent is 5(6)-mercapto-1H-benzo[d]imidazole-2-carboxamide. In another embodiment, the reagent is 4-mercapto benzoic acid.

In another embodiment, the reagent is octanethiol.

In another embodiment, the reagents are selected from epoxy, "PEG-like" methoxyethyene glycol, amine, carboxylic acid, and aldehyde.

According to another embodiment, the present disclosure provides a device for sensing biomolecules comprising: (a) a chip as defined herein; and (b) an integrated circuit configured to detect an electrical current between the first and second electrodes upon passage of the biomolecule through the nanogap.

In one aspect of this embodiment, the device further comprises a detector for measuring the electrical current. The electrical current may be between the first and second electrodes upon passage of a biomolecule through the nanogap. Alternatively, the electrical current may be between the first and second fluid chambers upon passage of a biomolecule through the nanogap.

In another aspect of this embodiment, the device further comprises a system for introducing and removing solutions from the first and second fluid chambers. Solutions may be used to introduce a sample comprising a biomolecule to the first and second fluid chambers, and to wash or prepare the first and second fluid chambers before or after the sample has been introduced.

In another aspect of this embodiment, the device further comprises a system for analyzing the electrical current.

Fabrication Procedures According to One or More Exemplary Embodiments

In certain embodiments, the fabrication of the assay chip begins with the construction of relatively large (100 nm-1 μm) electrode gaps in a confined layered structure by standard lithography techniques (FIG. 3A-FIG. 3C). Specifically, and as shown in FIG. 3A, metal alignment marks (Au/Cr 30 nm/2 nm) are first patterned on a chip by a standard photolithography, metallization and lift-off process to allow the succeeding layers to align with each other. Next, the initial (100 nm-1 μm gap) electrode pairs (3) (and conducting lines/contact pads for interfacing with electronics) are patterned with the same process (Au/Cr 50 nm/2 nm). Next, a first sacrificial layer (8) (5-10 nm Cr, Ni or any other material that can be chemically etched away without harming the initial electrodes) is deposited over the gap between the electrode pair (3). The first sacrificial layer defines the height of the final nanopore channel. In alternate fabrication embodiments, the first sacrificial layer is deposited prior to deposition of the initial electrode pairs, which are deposited on top of the sacrificial layer.

Next, the entire chip is coated with a passivation layer (9). The passivation layer comprises silicon dioxide, silicon nitride, hafnium oxide, zirconium dioxide, aluminum oxide, titanium oxide, SU-8 polymer, or other dielectric materials that are resistive to the etching process of sacrificial layers, and combinations thereof. It is prepared, e.g., by applying a coating of about 100 nm to about 200 nm thick silicon dioxide by or about 50 nm to about 100 nm hafnium oxide by atomic layer deposition, isolating all the metal surfaces, followed by 500 nm-2 μm photoresist (SU-8 polymer) by photolithography which has open windows that overlap with the first sacrificial layer (8). Next, the silicon oxide layer of the passivation layer is etched with a 20:1 diluted buffered oxide etchant, or hafnium oxide layer is etched by reactive ion etching process, through the open windows of the photoresist layer to expose the first sacrificial layer below. Finally, the first and second fluid chambers are constructed over these multilayer devices by standard soft-lithography of polydimethylsiloxane (PDMS) to finish the starter-kit chip.

In another embodiment, the assay chip comprises a second and a third fluid channels, which are constructed from a second sacrificial layer (FIG. 4A-4E). In this embodiment, the first sacrificial layer is disposed in between a first and a second region of the second sacrificial layer.

In one aspect of this embodiment, the first and second sacrificial layers are disposed on top of the substrate. In the first aspect of this embodiment, following fabrication procedures similar to that described above, and after the first sacrificial layer is defined, a second sacrificial layer region with translocation guidance canals structure is constructed adjacent to the first sacrificial layer, such that the first sacrificial layer is disposed between a first region and a second region of the second sacrificial layer. The second sacrificial layer is defined by lithography and deposition of a second material on top of the substrate. The second material that can be used as the second sacrificial layer can be the same as the first sacrificial layer, but preferably can be a material that can be etched separately without affecting the first sacrificial layer or the passivation layer, with relatively fast etching rates (>about 1 μm/min). In some embodiments, the second material is Mg. In some aspects of this embodiment, the second material is Mg deposited to a thickness of about 50 nm to about 300 nm. The supporting walls of the translocation guidance canals are constructed by additional lithographic patterning of dielectric materials or polymers such as SU8, silicon dioxide, silicon nitride, hafnium oxide, zirconium dioxide, aluminum oxide, titanium oxide, SU-8 polymer and combinations thereof. (FIG. 4A, FIG. 4B, and FIG. 4C)

Figure 4E:
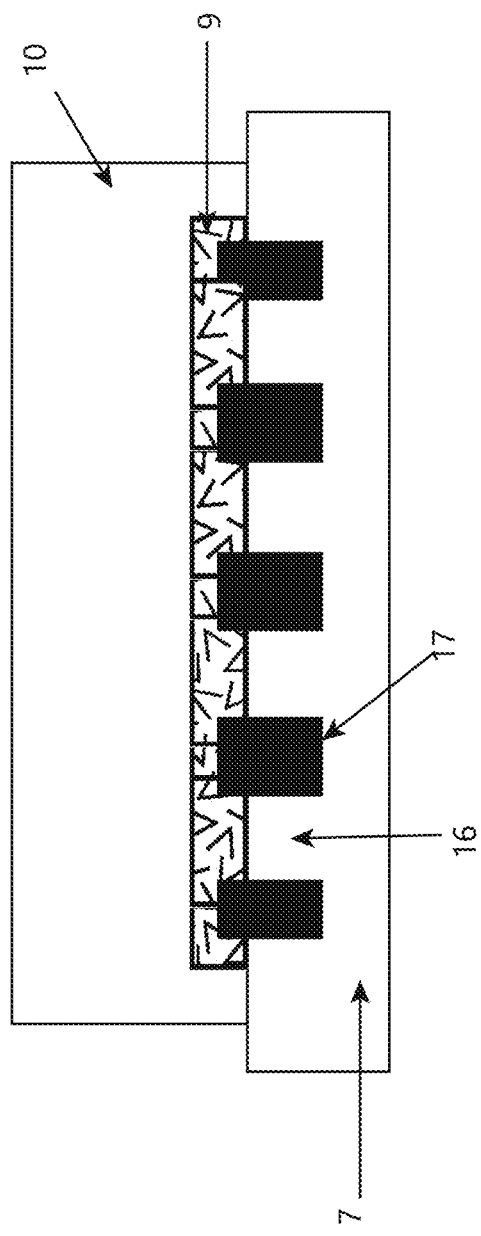
FIG. 4E shows the cross-section schematic diagram of the starter-kit chip across line (15) of FIG. 4A, according to the second aspect of this embodiment, before etching of the first and second sacrificial layers, showing (10) PDMS layer, (9) passivation layer, (7) substrate, (17) second sacrificial layer, and (16) plurality of supporting walls defined by lithography and etching of the substrate.

In a second aspect of this embodiment, the second sacrificial layer is disposed partially on top of the substrate. In this second aspect, the second sacrificial layer with translocation guidance canals is constructed by first patterned etching down into the substrate (typical depth of the etching is, but not limited to, about 50 nm to about 500 nm), and then refilling the etched trenches with a second material with comparable or larger thickness to form a continuous connection with the first sacrificial layer. The second material is as described in the preceding paragraph, This thickness of the second sacrificial layer is about 50 nm to about 500 nm. The plurality of supporting walls of the translocation guidance canals are formed directly as the remaining vertical structure of the substrate during the etching process. (FIG. 4A, FIG. 4D, and FIG. 4E)

In certain embodiments, before sequencing experiments, the primed chip can be prepared as follows. The sacrificial layer (8) of the starter kit chip is first etched by an appropriate etchant, such as chromium or nickel etchant through openings in the passivation layer (FIG. 2B). The etchant will eventually create a first fluid channel that (a) is connected to the first and second fluid chambers, and (b) passes through a gap between the electrode tips. The height of the fluid channel (and therefore of the eventual nanopore) will be equal to the original thickness of the first sacrificial layer.

From the primed chip, the assay chip is prepared as follows. The first and second fluid chambers are filled with an electrochemical solution for Au, Pd or Pt deposition. The type of metal used in the deposition step depends on the type of biomolecule to be detected or sequenced. When depositing Au, the electrochemical solution comprises 17.5 mM potassium gold cyanide, $KAu(CN)_2$ and 186 mM potassium citrate, $K_3C_6H_5O_7$.

Figure 5:
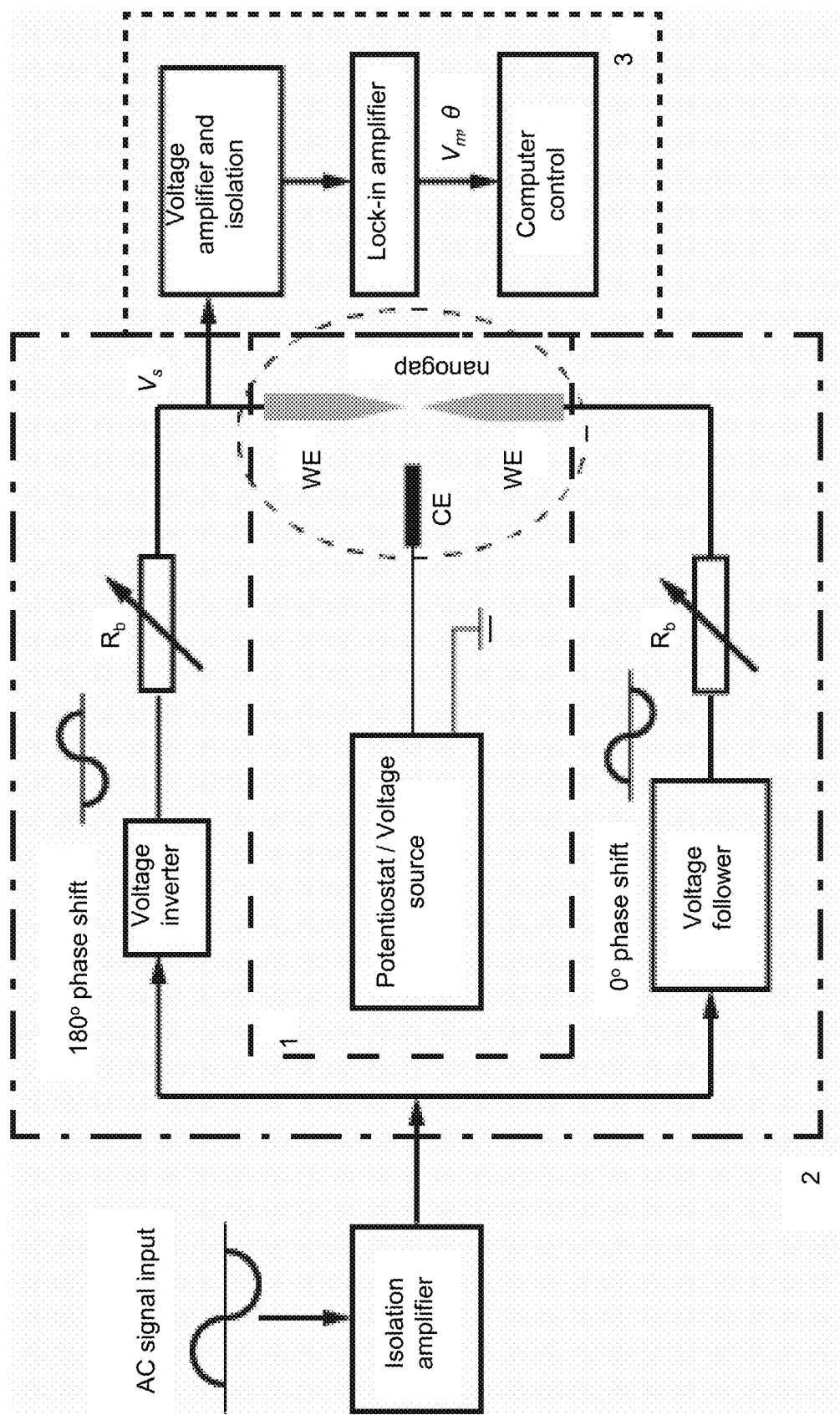
FIG. 5 shows a schematic diagram of an electrochemical deposition and feedback control circuit according to an embodiment of the present disclosure. In certain embodiments, deposition is performed by a two-electrode electrochemical cell (1) in which a Ag/AgCl electrode serves as the counter electrode (CE) and the nanogap tips are the working electrodes (WE). The impedance between the nanogap tips is monitored by an AC circuit (2), where the AC potential at one of the electrodes is analyzed by a lock-in amplifier so that a computer program (3) can calculate the corresponding impedance between the electrodes, and use it to control the metal deposition in real time.

A potential bias typically between about +1000 mV to about −1000 mV is applied to both metal electrodes, which serve as the working electrodes (WE) in FIG. 5, relative to a Ag/AgCl electrode (CE), to start deposition of metal onto both the electrode tips.

In alternate embodiments, a three-electrode configuration (i.e., a WE, CE and reference electrode configuration) is adapted where an additional reference electrode is used to more accurately regulate the potential of the WE.

Figure 6:
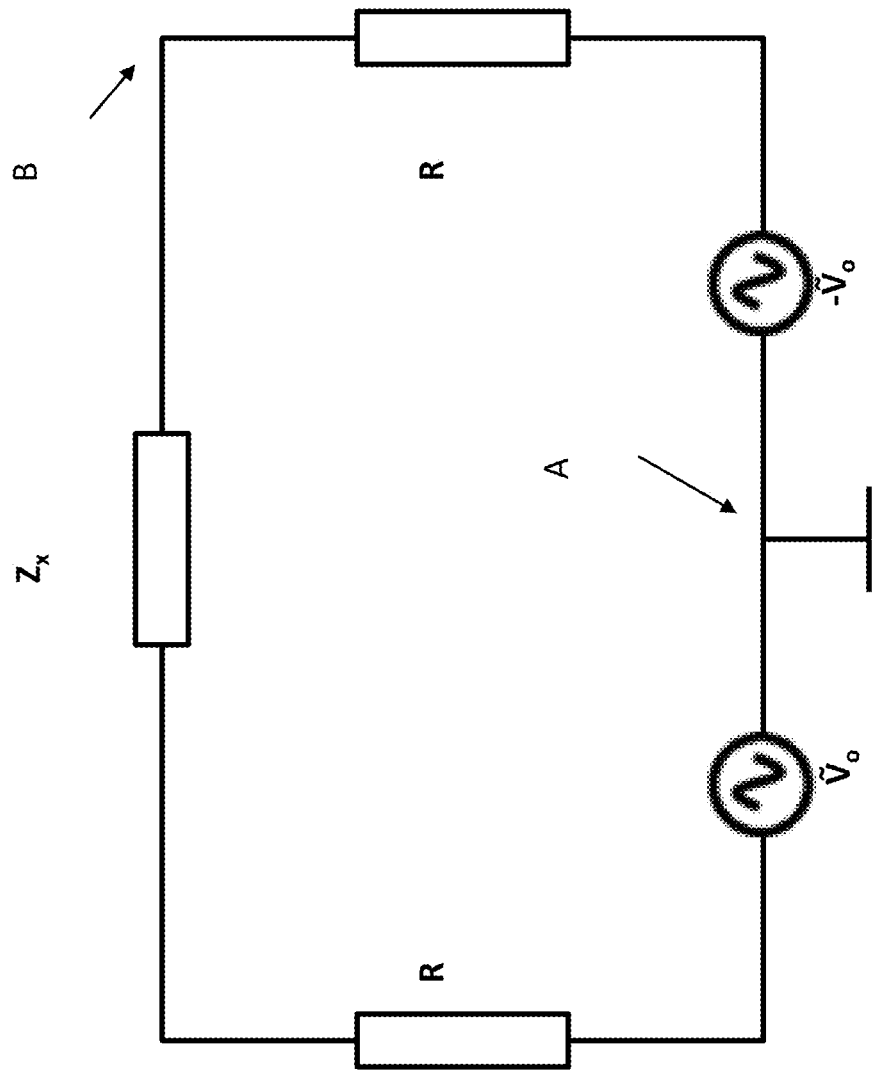
FIG. 6 shows a schematic diagram of the equivalent circuit and analysis for impedance measurement. $\tilde{V}$ and $-\tilde{V}$ are AC voltage sources with 180° phase difference. $Z_x$ is the impedance between the electrode tips. The AC voltage $V_{AB}$ is measured between points A and B. Resistor R can be tuned to change the most sensitive range of impedance that the system can detect for optimal distance control. Typical value of R is between 5 KOhm and 1 MOhm.
Figure 7:
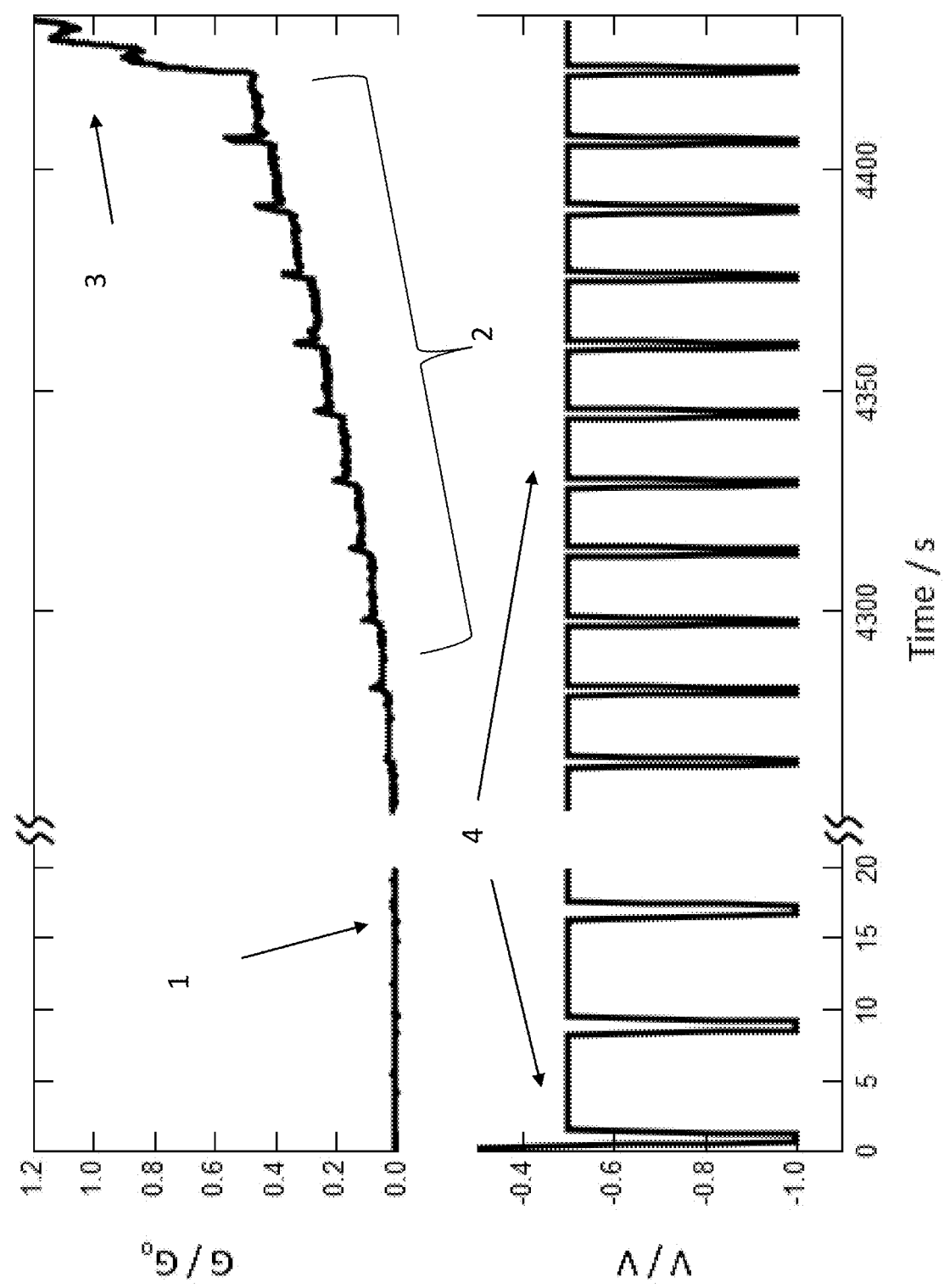
FIG. 7 shows exemplary conductance signals from the impedance monitor circuit and the potential output from the potentiostat/voltage source during a deposition. Several key components are highlighted as: (1) conductance when the electrodes are still far from each other (open circuit conductance), (2) increasing conductance as electrode tips approach contact, (3) quantized conductance as electrode tips establish point quantum contact, and (4) voltage pulses applied at the electrodes, where the deposition of metal is enabled during the negative peaks.
Figures 8A, 8B:
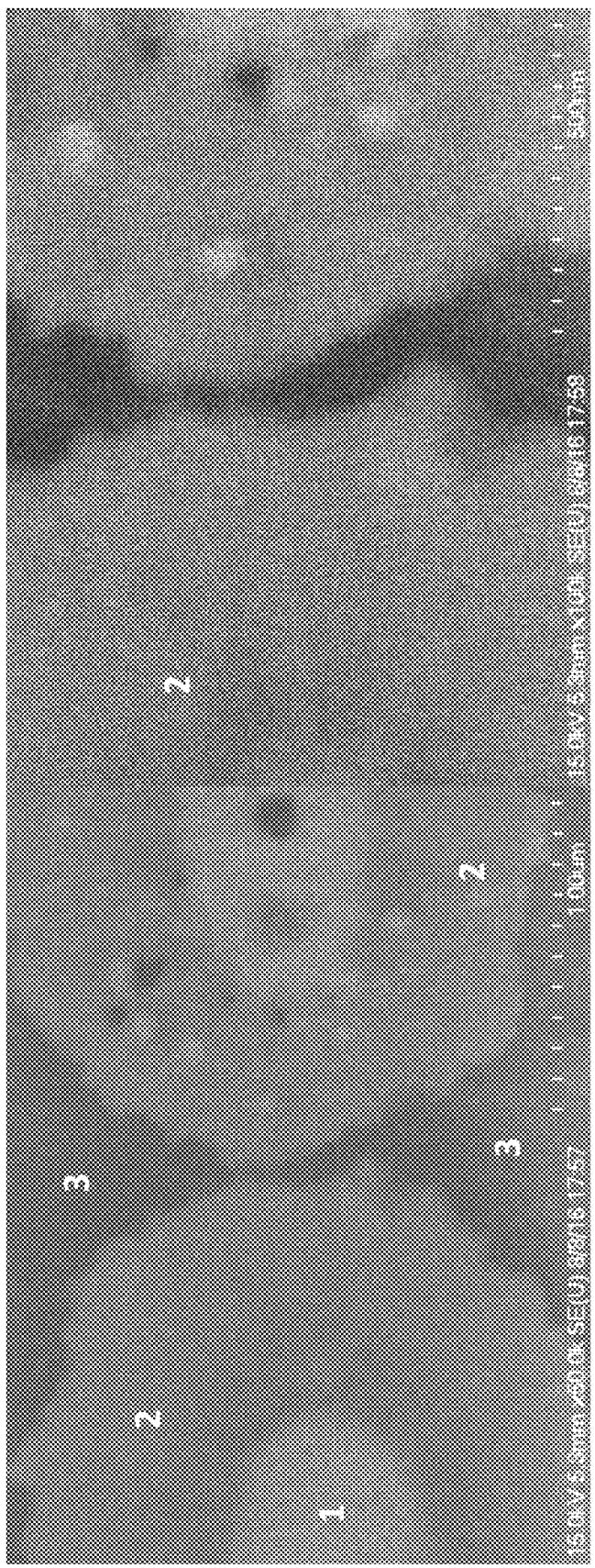
FIG. 8A shows a Scanning Electron Microscope (SEM) top-view image of the first and second electrodes of an assay chip according to an embodiment of the present disclosure after formation of the nanopore channel showing (1) initial electrode tips, (2) electrochemically deposited metal within the confined space between the dielectric surfaces, and (3) fluid channel connecting to chambers.
FIG. 8B shows a zoom in of the SEM image showing detailed dimensions of the nanopore channel of <about 20 nm wide. The width of the nanopore can be linearly tuned by controlling the deposition time from about 20 nm to <about 1 nm. The thickness of the deposited metal is limited by the confinement to about 10 nm.

The metal deposition is bounded between the chip substrate and the silicon dioxide layer, and the impedance between the metal electrodes is monitored by an independent AC circuit. (FIGS. 5 and 6). The output voltage of the AC circuit has a simple dependence on the impedance as shown in the equivalent circuit and equation in FIG. 6. A real-time control program is used to control the deposition so that the size of the gap can be finely tuned based on the impedance. In practice, the best way to increase the accuracy of such control is to use pulsed deposition potentials instead of a continuous bias, indicated in FIG. 7 as (4). The metal will only deposit during the short period of a negative bias pulse, and for each pulse, the gap is estimated to decrease by about 0.1 nm to about 0.2 nm on average. FIG. 7 shows the gap conductance as a function of time for a device according to an embodiment of the present disclosure. The conductance stays near zero when the electrodes are far away from each other, then starts to increase pronouncedly as the distance between the tips enters a critical range close to about 30 nm. The conductance jumps to one or small integer multiples of the quantum conductance, $G_o=77$ μS when a point contact is formed between the electrode tips. Since the deposition increases linearly with the time/number of pulses, the detection of the first pronounced increase of conductance and the number of deposition pulses afterwards would result in a reproducible gap size with a resolution of about 0.1 nm to about 0.2 nm. FIG. 8A and FIG. 8B shows a preliminary result of a pair of gap of about 20 nm prepared by such control circuit. From the image the newly deposited metal within the confined space (<about 10 nm thick) can be clearly distinguished from the original pair of electrodes (>about 50 nm) defined by lithography. The lateral shape and size of the electrodes can be further optimized by tuning the electrochemical deposition conditions and reducing the starting gap size to below about 100 nm.

In certain embodiments, before sequencing experiments, the electrodes are modified by a reagent that is capable of selectively interacting with a unit of a biomolecule, e.g., is capable of forming hydrogen bonds with the biomolecule as it translocates through the assay chip. Such interaction can be used to slow down the translocation speed, as well as to provide recognition tunneling read out signals.

Operation of the Devices According to One or More Exemplary Embodiments

The present disclosure provides a method for detecting a biomolecule in a sample. In one embodiment, the method comprises (a) providing a device as described herein; (b) passing a biomolecule through a nanogap; and (c) detecting a signal produced when the biomolecule passes through the nanogap. In another embodiment, the method comprises (a) providing a device as described herein; (b) passing a biomolecule through a nanogap; and (c) detecting a signal produced when the biomolecule interacts with the first and second reagent.

The present disclosure also provides a method for sequencing a biomolecule. In one embodiment, the method comprises (a) providing a device as described herein; (b) passing a unit of the biomolecule through a nanogap; (c) detecting a signal produced when the unit of the biomolecule interacts with the first and second reagent; (d) from the signal detected in (c), identifying the unit of the biomolecule; (e) repeating steps (b) through (d); and (f) from the units identified in (d), determining the sequence of the biomolecule.

In the methods described in the preceding paragraphs, the biomolecule may be passed through the nanogap by applying a driving bias between the first and the second chamber.

In the methods described in the preceding paragraphs, the biomolecule may be passed through the nanogap by time-modulating the potential bias between the first and second electrodes of the device.

The signal detection of step comprises detecting an electrical current between the first and second electrodes in one embodiment and detecting the electrical current between the first and second fluid chambers in another embodiment.

Additional features and advantages are discussed below.

Figure 9:
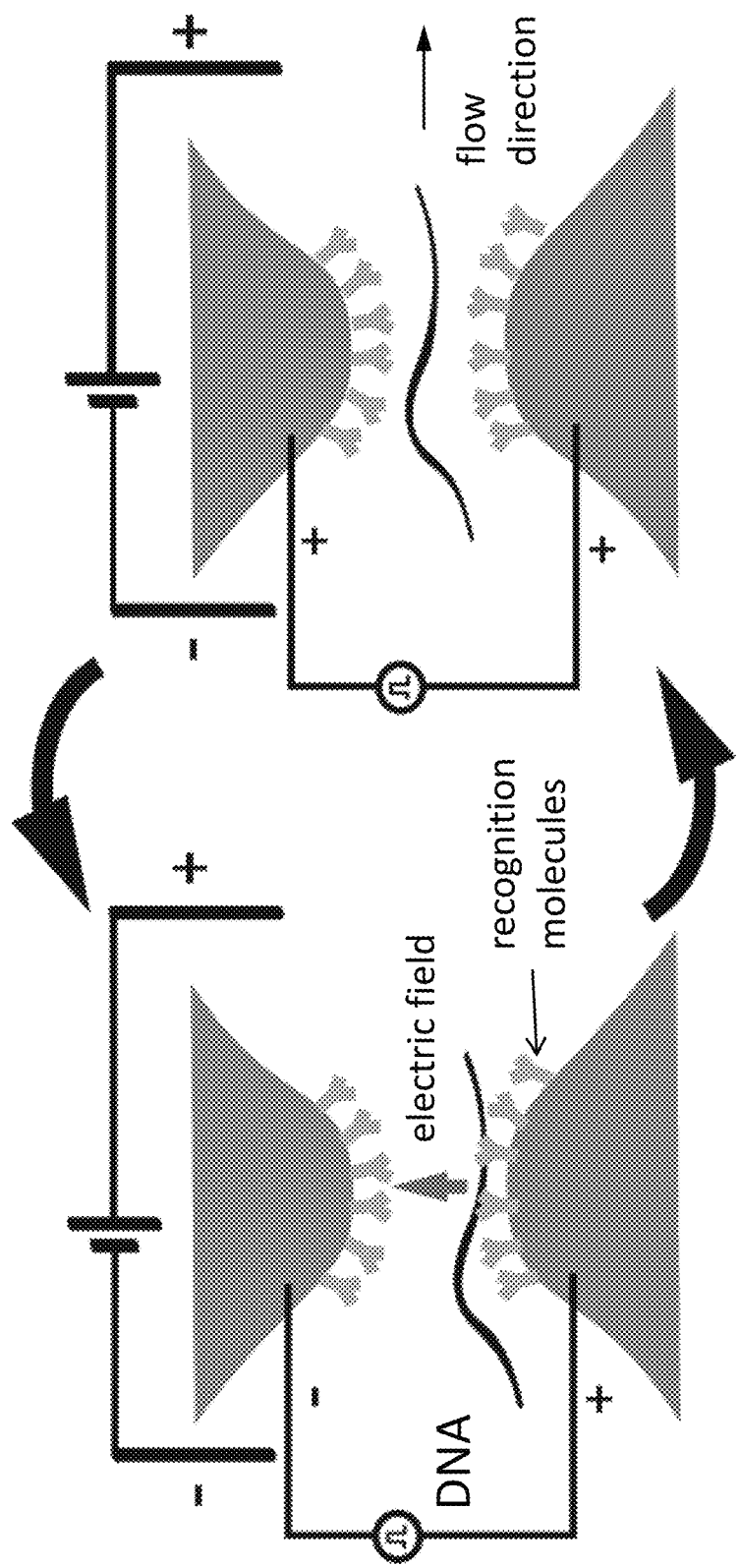
FIG. 9 shows a schematic diagram of method of controlling DNA translocation using electric field and surface functionalization between the electrodes according to an embodiment of the present disclosure. Left: Different polarities of bias are applied to the electrodes, which introduce a transverse electric field to push the DNA molecule against the positively biased electrode and the translocation is stopped by the enhanced interaction between the molecule and the surface of the electrode. Right: Bias of the same polarity is applied to both electrodes, which releases the DNA molecule to the center of the pore and helps to tune the strength of the electroosmotic flow that drives the DNA through the channel By alternating between these two modes using high-frequency pulses, the DNA molecule can move stepwise through the pore.

In certain embodiments, after the dimensions of the nanopore channel have been finalized, the devices are used in immediate sequencing experiments. The embedded electrodes aligned with the nanopore channel allow a method to control the translocation of the DNA molecule. Specifically, theoretical modeling suggests that for a driving bias of about 0.1V across a 6.4 nm thick nanochannel, a uniform transverse electric field of 180 mV/nm could completely stop the translocation of the DNA molecule based on the van-der-Waals interaction with the side wall [1]. In addition, 400-fold decrease of DNA translocation speed was observed experimentally with a nominal transverse field of 10 mV/nm between a pair of metal electrodes of about 15 nm thick sealed in a about 60 nm high nanochannel [2], although effective control of the translocation has never been achieved. We note that in our design a sharp tip with radius <about 50 nm will bring >about 10× field enhancement to the field at the gap resulting in a reduction of applied bias [3], which allows a much stronger control over the molecule-nanopore interactions in our device and enables new modes for the molecule to maneuver through the nanopore channel Specifically, the translocation speed of DNA molecule through an about 20 $nm^2$ solid-state nanopore is about $10^5$ bases/ms [4]. As a rough estimation, to reduce the translocation speed to below 1000 bases/ms just by electric field, a transverse bias between about 20 mV and about 360 mV for a gap size of about 2 nm is needed. Given the cyclic voltammetry results for Pt/Pd/Au electrodes in PBS buffer, there is a safe electrochemical window between about −50 mV and about +200 mV vs Ag/AgCl reference. Therefore, the integrated transverse electrodes will be able to switch between two potential configurations within the safe range as shown in FIG. 9A: (i) both electrodes can be held at the same potential (FIG. 9 right), where the Debye length is tuned to match the dimension of the nanopore, and the overlapping electric double layer (EDL) of DNA molecule and the nanopore will be tuned to facilitate the translocation [5,6]; (ii) polarized electric field can be applied between the electrodes (FIG. 9 left), where the negatively charged DNA chain will be pushed toward one side of the nanopore, resulting in a stronger DNA-electrode interaction and appreciable slowing down or a complete stop of the molecule [1,2]. By modulating the potential bias between the electrodes, the DNA can be "stepped" through the gap and achieve greater precision in position control and stability in readout signals. Advantageously, the modulation of potential bias between the electrodes, in addition to the modulation of the driving potential between the fluid chambers are not limited to the proposed pattern above but can be freely tuned and combined for optimal capturing of the molecule into the nanopore device, as well as optimal control of the translocation motion of the molecule, as uniquely enabled by the design of the device according to the present disclosure. The recognition tunneling readout can be achieved by surface modification of the metal electrodes using recognition molecules and tunneling current measurement as the DNA molecules translocate through the channel [7,8 and U.S. Pat. Nos. 8,961,757; 8,968,540].

Figure 10A:
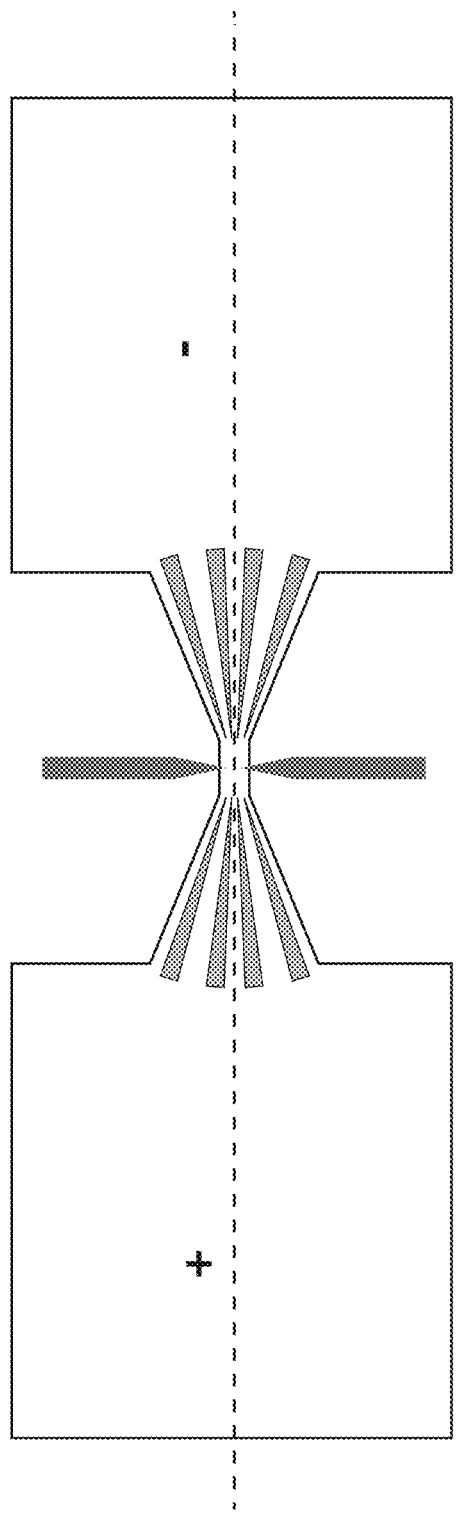
FIG. 10A and FIG. 10B show an engineered potential profile according to an embodiment of the present disclosure (FIG. 10B) along the cross-sectional line through the nanofluidic channels and the nanopore device (FIG. 10A). The potential gradient in the second sacrificial layer region increases the rate of biomolecule capture.
Figure 10B:
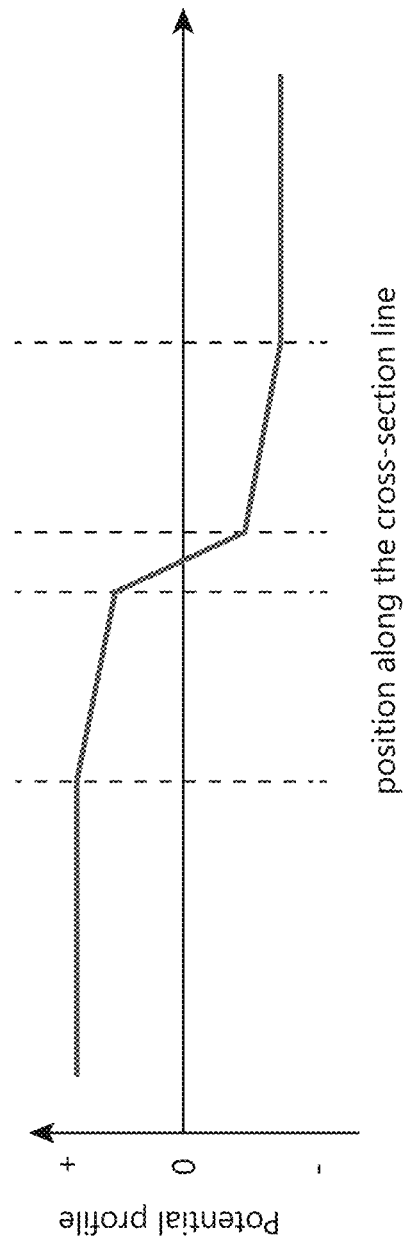
Figure 11:
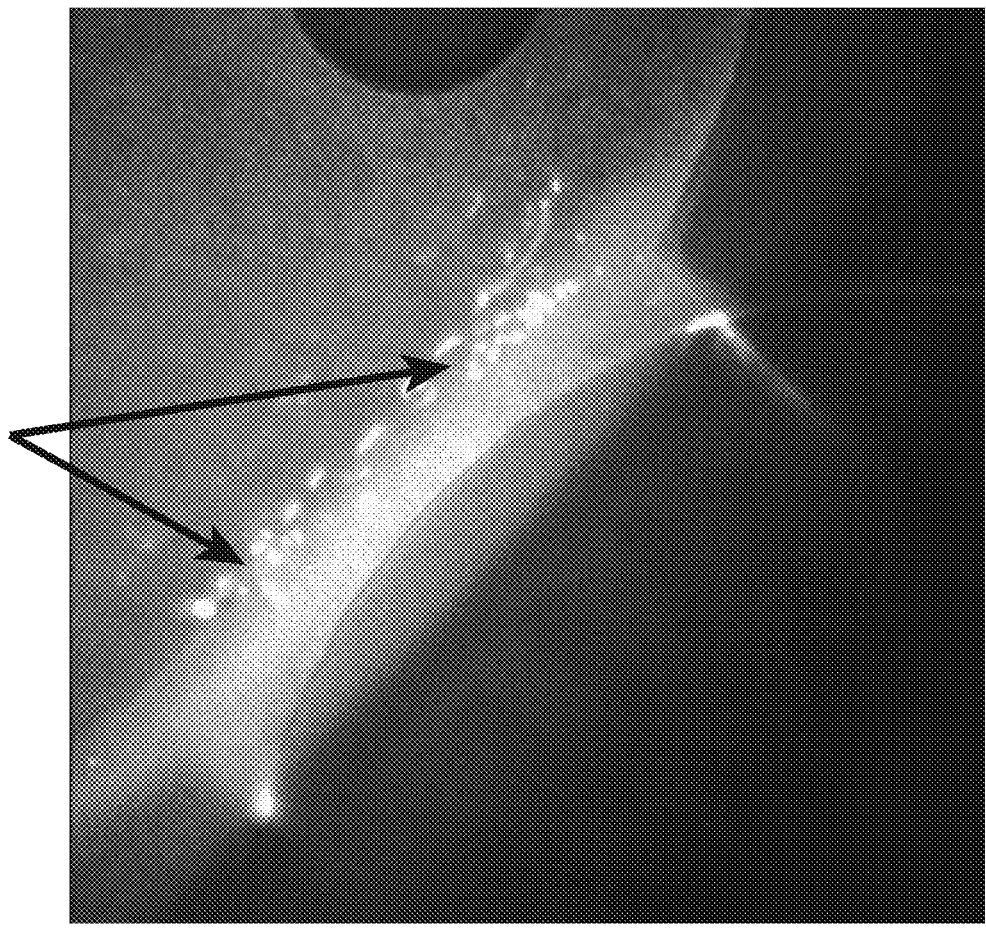
FIG. 11 shows an epifluorescence image of a device according to an embodiment of the present disclosure in which the second and third fluid channels with translocation guidance canals are defined by the second sacrificial layer. The DNA molecules are enriched at the entrance of the nanofluidic channel.

In embodiments in which the device comprises a second sacrificial layer and supporting wall structure, the etching of the second sacrificial layer results in translocation guidance canals, which is an engineered nanofluidic system connected directly to the nanopore device. This design can increase the capturing rate (the number of molecules captured by the nanopore device per unit time due to the driving potential across the chambers), due to the specially designed potential profile across the chambers as shown in FIG. 10. Specifically, the non-trivial potential drop at the opening of the second sacrificial layer region (much larger than the nanopore) can enrich and promote more biomolecules to enter the channel and eventually fall into the nanopore device with the help of the translocation guidance canals, as shown in FIG. 11. In contrast, for conventional nanopore devices where the nanopore is in contact directly with bulk volume of medium, the DNA molecules in the medium are mostly in Brownian motion until they accidentally get close to the nanopore within a distance comparable to its diameter, only where they begin to "feel" a decent potential drop to be captured for translocation through the nanopore.

Figure 12:
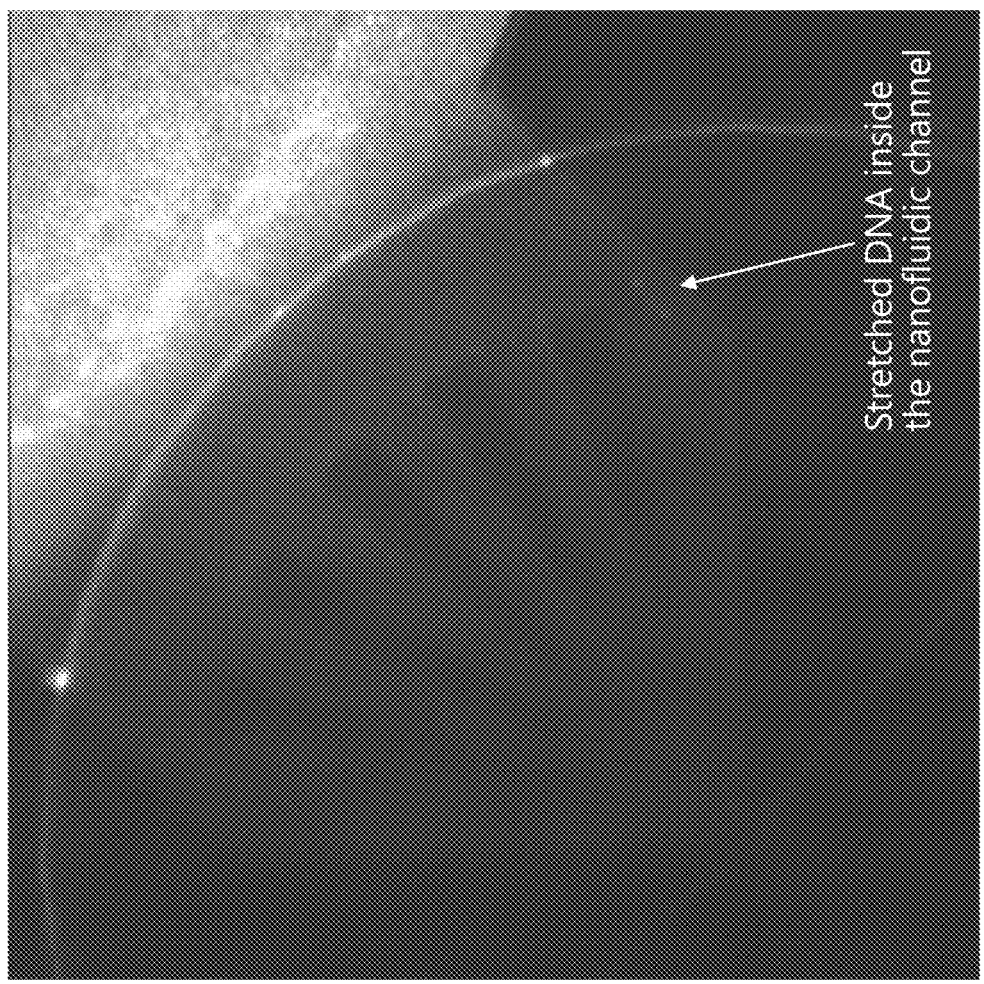
FIG. 12 shows a Total Internal Reflection Fluorescence (TIRF) image of a device according to an embodiment of the present disclosure in which the second and third fluid channels with translocation guidance canals are defined by the second sacrificial layer. The DNA molecule is stretched into linear shape as it moves through the nanofluidic channel, and the moving speed of the DNA molecule is significantly slowed.

The engineered nanofluidic system of this device can also help to slow down translocation, and to stretch the biomolecules into a linear shape as preferred for translocation before they reach the nanopore, as demonstrated in FIG. 12.

REFERENCES

The following references are hereby incorporated by reference in their entireties:
1. Luan, B., Wang, C., Royyuru, A., Stolovitzky, G. Controlling the motion of DNA in a nanochannel with transversal alternating electric voltages. Nanotechnology 2014, 25, 265101.
2. Tsutsui, M., et al. Transverse electric field dragging of DNA in a nanochannel Sci. Rep. 2012, 2, 394.
3. Tsujino, S. et al. Static and optical field enhancement in metallic nanotips studies by two-photon photoemission microscopy and spectroscopy excited by picosecond laser pulses. Appl. Phys. Lett. 2009, 94, 093508.
4. Akahori, R. et al. Slowing single-stranded DNA translocation through a solid-state nanopore by decreasing the nanopore diameter. Nanotechnology 2014, 25, 275501.
5. He, Y. H., et al. Controlling DNA translocation through gate modulation of nanopore wall surface charges. ACS Nano 2011, 5 (7), 5509-5518.

6. Nam, S. W., Rooks, M. J., Kim, K. B., Rossnagel, S. M. Ionic field effect transistors with sub-10 nm multiple nanopores. Nano Lett. 2009, 9, 5, 2044-2048.
7. He, J., Lin, L., Zhang, P., Lindsay, S. Identification of DNA basepairing via tunnel-current decay. Nano Lett. 2007, 7, 12, 3854-3858.
8. Chang, S., Huang, S., He, J., Liang, F., Zhang, P., Li, S., Lindsay, S. Electronic signatures of all four DNA nucleosides in a tunneling gap. Nano Lett. 2010, 10, 3, 1070-1075.

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present invention. Accordingly, the present invention is not limited to the specific embodiments illustrated herein.

What is claimed is:

1. An assay chip comprising
   (a) a substrate;
   (b) a first and second fluid chamber;
   (c) a first fluid channel connecting the first and second fluid chamber, the first fluid channel being planar with the substrate;
   (d) a first and second electrode disposed on a top surface of the substrate and in the first fluid channel, located between the first and second fluid chamber, and having a nanogap therebetween, wherein the width of the nanogap is configured to be modulated by a confined electrochemical deposition process; and
   (e) a passivation layer disposed on respective top surfaces of the first and second electrodes and on top of the first fluid channel such that the nanogap is between the substrate and the passivation layer,
   wherein the passivation layer directly contacts the respective top surfaces of the first and second electrodes at the nanogap and extends over the nanogap between the respective top surfaces of first and second electrodes to confine a top of the nanogap.

2. The assay chip of claim 1, further comprising
   (f) a second and third fluid channel, each having a plurality of translocation guidance canals, wherein the second fluid channel connects the first fluid chamber to the first fluid channel and the third fluid channel connects the second fluid chamber to the first fluid channel; and
   wherein the passivation layer is disposed on top of the first and second electrodes and the first, second, and third fluid channels.

3. The chip of claim 2, wherein the nanogap has a width of about 1 nm to about 20 nm.

4. The chip of claim 2, wherein the substrate is a coated glass substrate.

5. The chip of claim 2, wherein the first and second fluid chamber comprise a material selected from the group consisting of polydimethylsiloxane, epoxy, silica and combinations thereof.

6. The chip of claim 2, wherein the first and second electrode comprise gold, platinum or palladium.

7. The chip of claim 2, wherein the passivation layer comprises a material selected from the group consisting of silicon dioxide, silicon nitride, hafnium oxide, zirconium dioxide, aluminum oxide, titanium oxide, SU-8 polymer, and combinations thereof.

8. The chip of claim 2, wherein a first reagent is attached to the first electrode and a second reagent is attached to the second electrode, wherein the first and the second reagent are capable of interacting with a biomolecule.

9. The chip of claim 1, wherein the chip is configured to modulate the width of the nanogap by applying a reversible bias between the first and second electrodes and a counter electrode.

* * * * *